US012588872B2

(12) United States Patent
    Watanabe

(10) Patent No.: US 12,588,872 B2
(45) Date of Patent: Mar. 31, 2026

(54) WEARABLE DEVICE, HEALTH MANAGEMENT SYSTEM AND HEALTH MANAGEMENT METHOD

(71) Applicant: SOXAI INC., Kanagawa (JP)

(72) Inventor: Tatsuhiko Watanabe, Yokohama (JP)

(73) Assignee: SOXAI INC., Yokohama (JP)

( * ) Notice: Subject to any disclaimer, the term of this patent is extended or adjusted under 35 U.S.C. 154(b) by 569 days.

(21) Appl. No.: 18/098,273

(22) Filed: Jan. 18, 2023

(65) Prior Publication Data

US 2024/0090835 A1    Mar. 21, 2024

(30) Foreign Application Priority Data

Sep. 9, 2022    (JP) ................................. 2022-144167

(51) Int. Cl.
    *A61B 5/00*         (2006.01)
    *A61B 5/0205*       (2006.01)
    *G02B 5/08*         (2006.01)
    *G02B 5/10*         (2006.01)
(52) U.S. Cl.
    CPC .......... *A61B 5/6826* (2013.01); *A61B 5/0059* (2013.01); *A61B 5/0205* (2013.01); *G02B 5/0808* (2013.01); *G02B 5/10* (2013.01)
(58) Field of Classification Search
    CPC . A61B 5/1455; A61B 5/14552; A61B 5/6826; A61B 5/0205; A61B 5/02416
    See application file for complete search history.

(56) References Cited

U.S. PATENT DOCUMENTS

| | | | | |
|---|---|---|---|---|
| 5,964,701 A * | 10/1999 | Asada | .................. | A61B 5/6826 |
| | | | | 600/300 |
| 6,402,690 B1 * | 6/2002 | Rhee | .................. | A61B 5/02427 |
| | | | | 600/323 |
| 9,113,795 B2 * | 8/2015 | Hong | ................... | A61B 5/0205 |
| 10,015,582 B2 * | 7/2018 | Wagner | ................ | A61B 5/1455 |
| 10,076,253 B2 * | 9/2018 | Just | .................... | A61B 5/14552 |
| 10,126,779 B2 | 11/2018 | von Badinski et al. | | |
| 10,813,578 B1 * | 10/2020 | Ben Ishay | ............ | A61B 5/1455 |
| 11,324,292 B2 * | 5/2022 | Min | ................... | A61B 5/02416 |

FOREIGN PATENT DOCUMENTS

JP          2017-506376 A        3/2017

* cited by examiner

*Primary Examiner* — Eric F Winakur
(74) *Attorney, Agent, or Firm* — Maschoff Brennan

(57)          ABSTRACT

A wearable device to accurately detect biometric information of the user. The wearable device includes a ring body; a light emitting element which is disposed in the ring body, and is configured to emit light toward a center side of a ring; and a first optical element which is disposed in the ring body to be closer to the center side of the ring than the light emitting element, and is configured to change a direction of travel of the light to a direction narrowing a directional angle of the light. The ring body includes a protrusion on an inner peripheral surface of the ring body where the first optical element is disposed, and the protrusion is formed to protrude closer to the center side of the ring than another part of the inner peripheral surface where the first optical element is not disposed.

21 Claims, 17 Drawing Sheets

WEARABLE DEVICE, HEALTH MANAGEMENT SYSTEM AND HEALTH MANAGEMENT METHOD

CROSS REFERENCE TO RELATED APPLICATIONS

This application claims the benefit of priority to Japanese Patent Application No. 2022-144167 filed on Sep. 9, 2022. The entire contents of this application are hereby incorporated herein by reference.

TECHNICAL FIELD

The present disclosure relates to a wearable device, a health management system and a health management method.

BACKGROUND

With respect to the background art, there is Japanese Unexamined Patent Application Publication (Translation of PCT Application) No. 2017-506376 (which is hereinafter referred as Patent Document 1) on this technical field. Patent Document 1 discloses "(t)he WCD ("WCD" is an abbreviation of "wearable computing device") comprising an interior wall, an exterior wall, a flexible printed circuit board disposed between the interior wall and the exterior wall, and at least one component disposed on the flexible printed circuit board, wherein at least one of the interior wall and the exterior wall defines a window that facilitates at least one of data transmission, battery recharge, and status indication" (see abstract of Patent Document 1).

SUMMARY

Referring to paragraph 0223 of the Patent Document 1, it is disclosed that the base assembly comprises an optical element 1790 positioned adjacent to the concentrated light source 1770 for focusing the light emitting diode light onto the CPV ("CPV" is an abbreviation of "concentrated photovoltaic") inside the WCD. However, a configuration for accurately detecting biometric information of the user of the WCD is not disclosed concretely in the Patent Document 1.

Accordingly, it is an object of the disclosure to provide a wearable device, a health management system and a health management method for more accurately detecting biometric information of the user.

To solve the above-mentioned problems, for example, the configuration described in the claims is applied. The present disclosure includes a plurality of means for solving the above-mentioned problems, one example is a wearable device, which comprises: a ring body having a ring shape; a light emitting element which is disposed in the ring body, and is configured to emit light toward a center side of a ring; and a first optical element which is disposed in the ring body to be closer to the center side of the ring than the light emitting element, and is configured to change a direction of travel of the light to a direction narrowing a directional angle of the light. The ring body includes a protrusion on an inner peripheral surface of the ring body where the first optical element is disposed, and the protrusion is more protruding to the center side of the ring than another part of the inner peripheral surface where the first optical element is not disposed.

According to the present disclosure, it becomes possible to provide a wearable device, a health management system and a health management method for more accurately detecting biometric information of the user. Problems, configurations, and effects except those mentioned above will be clarified by referring to the description of the following embodiments.

BRIEF DESCRIPTION OF THE DRAWINGS

FIG. 18 is an exploded perspective view of the jig 600 of FIG. 17;

DETAILED DESCRIPTION

Hereinafter, the present technology will be described with regard to a wearable device according to an embodiment referring to the figures as appropriate. Herein the term "wearable device" is interchangeable with other similar variations such as "wearable electronic device", "wearable computing device", etc. In each drawing, explanations on configurations having the same function may be omitted except giving reference numbers with respect to the configurations. Also, in some figures, common directions are indicated by using X-, Y- and Z-axes. In the present embodiment, the X-, Y- and Z-axes are perpendicular to each other. However, the common directions are not limited to this example.

[Wearable Devices]

Figure 1:
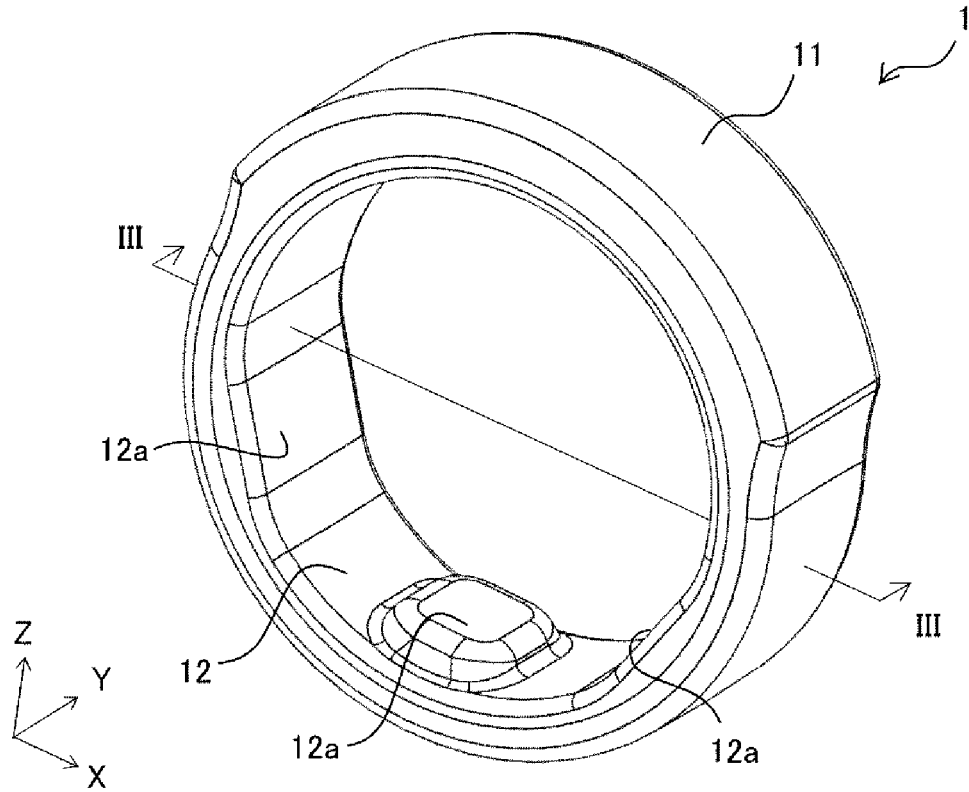
FIG. 1 is a perspective view of the wearable device 1 according to one embodiment.
Figure 2:
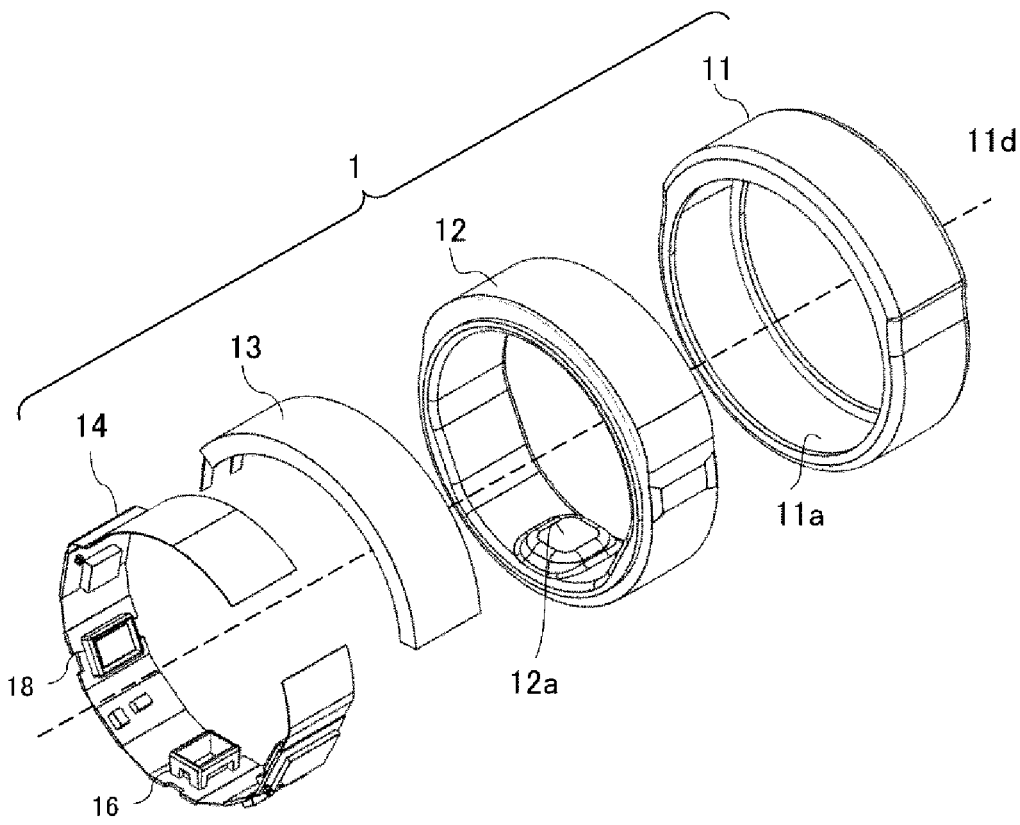
FIG. 2 is an exploded perspective view of the wearable device 1 according to one embodiment.
Figure 3:
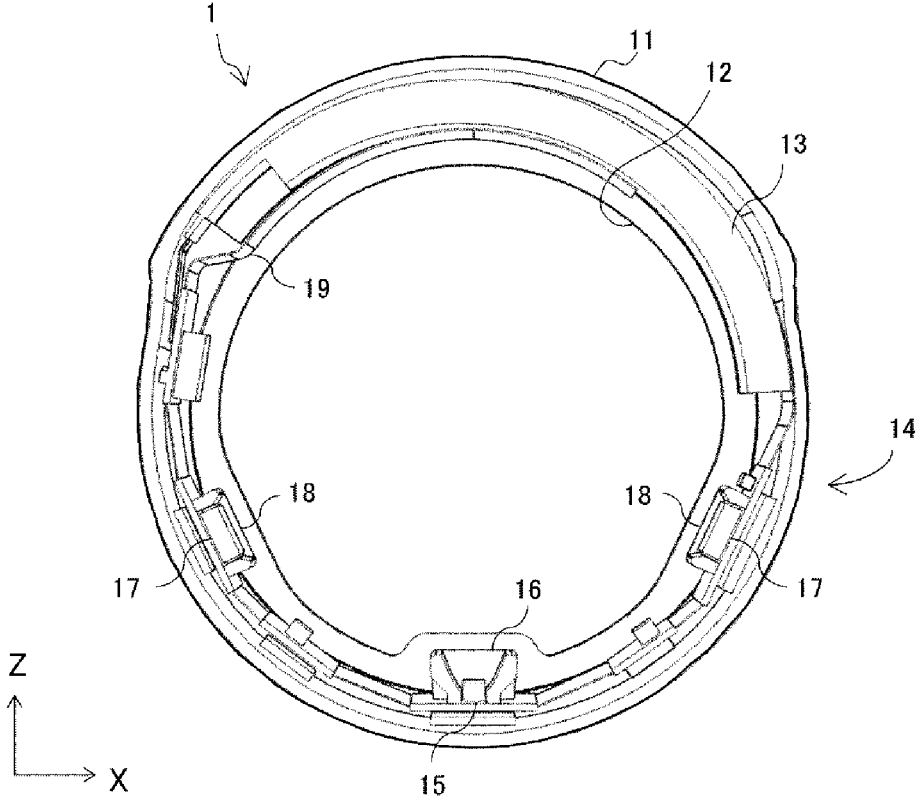
FIG. 3 is a cross-sectional view along line III-III in FIG. 1.
Figure 4:
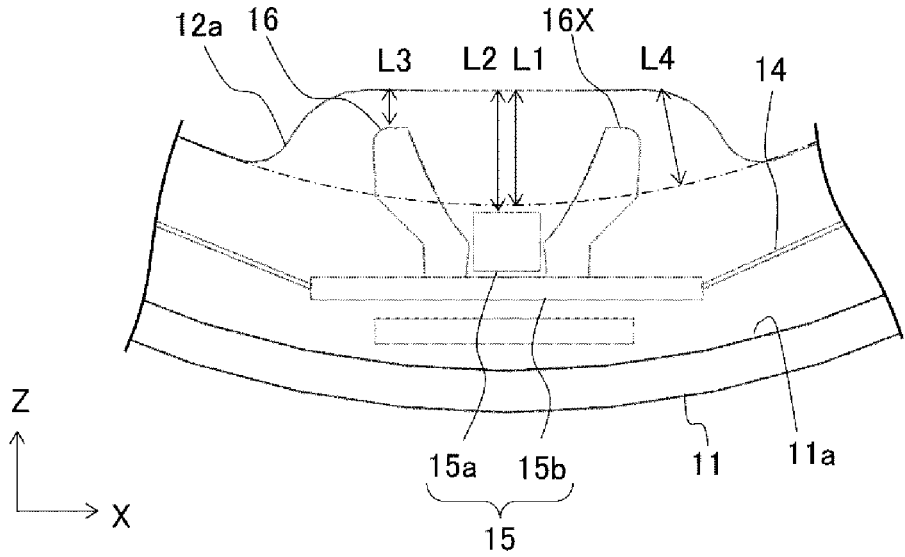
FIG. 4 is a partial enlarged view of FIG. 3.

FIGS. 1, 2 and 3 is respectively a perspective view of a wearable device 1 according to one embodiment, an exploded perspective view of the wearable device 1, and a cross-sectional view of the wearable device 1 along line III-III in FIG. 1. In addition, FIG. 4 depicts a partial enlarged view of FIG. 3.

In some embodiment, the wearable device 1 according to the present technology is configured as a device to be attached (which can also be paraphrased as "putted", "worn" and other similar variations) on a living body such as a human being in order to non-invasively acquire biological information of the living body.

The wearable device 1 according to one embodiment is configured to include a body 10 which has a ring shape (hereinafter, the "body 10" is referred as "ring body 10"), a light emitting element 15, and a first optical element 16. The body 10 is an element for attaching the light emitting element 15 and the first optical element 16 to a surface of a living body. Thus, the term "ring shape" with respect to the body 10 is not limited to a geometrically perfect circle, but may include, for example, shapes that can be considered generally circular, such as an approximately ring shape, nearly ring shape, almost completely ring shape, completely ring shape, etc. The body 10 may also has a closed or non-closed ring shape. As one of characteristics of the wearable device 1, the ring body 10 has a protrusion(s) 12$a$ at a part of an inner peripheral surface of the ring body 10, and the protrusion 12$a$ is formed to protrude more toward a center side of the ring compared with a part of the inner peripheral surface of the ring body 10 where the first optical element 16 is not disposed. Here, the term "center side" means the side opposite to the outside of the ring and is not necessarily limited to the direction toward the center of the ring. The "center side" means substantially in the direction toward the arterioles, described below, and may mean, for convenience in some embodiments, such as an approximately center of the ring, nearly center of the ring, almost completely center of the ring, completely center of the ring, etc., (hereinafter, the "substantially center of the ring" is referred as "center of the ring"). In some embodiments, if the body 10 is not perfectly circular, the center of the ring may be, for example, the center of gravity.

The wearable device 1 is also configured to be able to include the ring body 10, a light receiving element 17, and a second optical element 18. In some embodiments, the wearable device 1 is configured to include a combination of the light emitting element 15 and the light receiving element 17, and at least one of the light emitting element 15 and the light receiving element 17 is combined with the optical element 16, 18. It is possible to configure the wearable device 1 to include additional elements such as an electronic component 13, a wiring circuit board 14 and another electronic element 19.

Hereinafter, each the element will be described in order.

The ring body 10 may be annularly formed. On the whole, the ring body 10 constitutes an external shape of the wearable device 1. The ring body 10 may be a housing which is configured to store the elements such as the light emitting element 15, the first optical element 16, the light receiving element 17 and the second optical element 18 therein. In the embodiment, the ring body 10 is configured to include an exterior member 11 and a resin member for sealing one or more of elements (which is hereinafter abbreviated to sealing resin member) 12. In the figures, a central axis of the ring of the ring body 10 is illustrated to extend along the Y-axis direction.

The exterior member 11 may be annular in shape and may constitute a portion of an outer peripheral side of the ring body 10. For example, as depicted in FIG. 2, the exterior member 11 is provided with a recessed part 11$a$ on the center side of the ring. The recessed part 11$a$ is formed to be recessed toward the outer peripheral side (for example, it is formed in a concave shape). In consequence, the elements such as the light emitting element 15, the first optical element 16, the light receiving element 17 and the second optical element 18 are able to be arranged in the recessed part 11$a$. In some embodiments, the exterior member 11 may be configured to have a certain degree of strength and/or hardness to protect the elements from external force, etc. For example, the exterior member 11 may be composed of a metal material, a ceramic material, or a synthetic resin material which is high in strength (which may be configured, for example, to have a tensile strength of 30 N/mm² or more at 25° C.).

In some embodiments, example of the metal material constituting the exterior member 11 may include a metal such as titanium, tantalum, hafnium, zirconium, niobium gold, platinum etc., and an alloy thereof; and other less bioreactive material which is low in reactivity such as a surgical stainless steel. However, the metal material is not limited to these examples. These metal materials have low bioreactivity in addition to high intensity. In some embodiments, example of the ceramic material may include an oxide ceramic such as alumina, zirconia, yttria, etc.; a carbide ceramic such as silicon carbide, boron carbide, titanium carbide, zirconium carbide, etc.; a nitride ceramic such as aluminum nitride, silicon nitride, boron nitride, etc.; and a zirconium boride such as titanium diboride, tungsten boride, zirconium boride, etc. However, the ceramic material is not limited to these examples. The ceramic material is hard and have a different texture which differs from the metal material. Further, example of the resin material may include a general purpose plastic such as high-density polyethylene, polypropylene, acrylonitrile butadiene styrene (ABS), acrylic resins, etc.; an engineering plastic such as polyamide, polycarbonate, fiber-reinforced plastics, etc.; a super engineering plastic such as polyimide, polyamideimide, polyphenylene sulfide, etc.; and other biocompatibility plastics. However, the synthetic resin material is not limited to these examples. The resin material may be lightweight. For example, one kind of these materials may be used alone or as a composite of two or more.

The sealing resin member 12 has annularly in shape and constitutes a portion of an inner peripheral side (or center side) of the ring body 10. The sealing resin member 12 is configured to be integrally disposed on the center side of the exterior member 11. In consequence, the elements (such as the light emitting element 15, the first optical element 16, the light receiving element 17, and the second optical element 18) are able to be arranged in the recessed part 11$a$ to be hermetically and/or watertightly sealed. For example, the sealing resin member 12 may be formed integrally with the exterior member 11. Alternatively, for example, the sealing resin member 12 may be detachably configured with respect to the exterior member 11 by using a fixing member, a fixing means, etc.

The above-mentioned sealing resin member 12 may be configured by using the same resin material as the exterior member 11. However, for a part covering at least the light emitting element 15 and the light receiving element 17, the sealing resin member 12 may be formed of material(s) through which light emitted from the light emitting element 15 is transmissive to allow the propagation of light between the light emitting element 15 and the light receiving element 17. The transmissivity of light is not particularly limited. For example, a transmissivity for the light emitting element 15 may be 50% or more. In some embodiments, a transmissivity for the light emitting element 15 may be such as for example, 70% or more, such as 80% or more, or such as 90% or more. For example, the resin material for constituting the sealing resin member 12 may include a resin material such as an acrylic resin, styrene resin, polycarbonate resin, polyolefin resin, epoxy resin, etc. However, the resin material is not limited to these examples. In a case that the sealing resin member 12 is formed integrally with the exterior member 11, for example, the sealing resin member 12 may be constituted by a resin material such as a thermoplastic resin material, reactive curing-type thermosetting resin material, etc., which is able be formed by such as the casting and molding, injection molding, transfer molding, etc. For example, in some embodiments, a molding may be performed in a temperature range from normal temperature (e.g. about 20° C.) or at about 60° C., by using a reactive curing-type resin material having epoxy resin or phenoxy resin of bisphenol type (which is, typically, bisphenol A type or bisphenol F type) as a base polymer.

The size of the ring body 10 is not strictly limited, and may be appropriately sized according to an attaching part of a living body. In a case that the wearable device 1 is configured as a finger-ring type device, for example, it is exemplified to be annular with an inner diameter of about 13 mm or more and 30 mm or less. The approximate shape of the ring body 10 may be formed as a geometrically perfect circle, or may be formed as an annular shape, an elliptical shape, an oval shape, etc., which is considered to have a generally circular shape. In addition, the thickness of the ring body 10 (which corresponds to a size along a radius direction of the ring) may be generally uniform over the entire circumference. However, it is possible to change the thickness of the ring body 10, for example, by relatively thickening a thickness of a part which is disposed on a back of a hand and by relatively reducing a thickness of a part which is disposed between fingers or on a palm of a hand.

The light emitting element 15 is disposed in the ring body 10 and is configured to emit light toward the center side of the ring. The light emitting element 15 is typically a light source for constituting a light sensor in pairs with the light receiving element 17. As the light emitting device 15, for example, it is possible to use any one of various kinds of the light emitting diode (which is hereinafter abbreviated to LED), the semiconductor laser or the laser diode (which is abbreviated to LD), the organic/inorganic electroluminescence (which is abbreviated to EL), etc. For example, the LED may be used as the light-emitting device 15 in order to realize a high-precision measurement for targeting arterioles, which will be described later, with a small area or footprint. The wavelength of light emitted from the light emitting element 15 may be appropriately set in accordance with a target to be detected. For example, the light emitting element 15 may include one or more light emitting elements.

In a case that a plurality of light emitting elements are provided, each light emitting element may generate light having the same wavelength or different wavelengths.

The light receiving element 17 is disposed in the ring body 10 and is configured to detect light. The light receiving element 17 is typically a light detector for constituting a light sensor in pairs with the light emitting element 15. As the light receiving element 17, for example, it is possible to use any one of various kinds of photodiode (which is abbreviated to PD), phototransistor, photoconductive element, etc.

In some embodiments, the light emitting element 15 and the light receiving element 17 may be arranged such that an angle $\theta$ between line segments connecting the center of the ring to each of the light emitting element 15 and the light receiving element 17 is in a range of 55° or more and 90° or less, as will be described in detail below. In some embodiments, two light receiving elements 17 may be arranged so that one light emitting element 15 sandwiched between the two photodetectors 17.

In some embodiments, in view of increasing a detection accuracy, the angle $\theta$ may be 60° or more, 65° or more, or such as 70° or more. In addition, in some embodiments, the angle $\theta$ nay be 85° or less, 80° or less, or such as 75° or less.

The light emitting element 15 and the light receiving element 17 may constitute, for example, a "photoplethysmogram sensor" or "photoplethysmography sensor" (which is hereinafter abbreviated to PPG sensor). In photoplethysmography, a "blood volume pulse" corresponds to a temporal change in a volume of blood within a capillary caused by perfusion, provides biological information including information about heart rate and internal information of vessels. The incident light at visible region or near infrared region has such a characteristic that the light is able to be selectively absorbed by hemoglobins of red blood cells in biological tissues and also the light is able to be transmitted or reflected by other living tissues. According to the photoplethysmography, the blood volume pulse may be measured by making visible light or near infrared light enter into living tissues, and then by detecting the transmitted light or reflected light by using the PPG sensor. Various biological information may be obtained by analyzing "photoplethysmography signals" (which is hereinafter abbreviated to PPG signals) acquired by the PPG sensor. Hereinafter, the method for detecting the transmitted light is referred to as "transmission type method", and the method for detecting the reflected light (including the scattered light) is referred to as "reflection diffusion type method."

In some embodiments, the light emitting element 15 may include a plurality of light sources for detecting a plurality of biological information (for example, vital signs). In a case that the light emitting element 15 includes a plurality of light sources, each light source may be used in combination for the purpose of obtaining different biological information. The light emitting element 15 may be in a form of a chip. Alternatively, the light emitting element 15 may be in a form of a package in which one or more chips 15a or other elements are provided on a substrate 15b (see FIG. 4).

Specifically, for example, the light emitting device 15 may include a green LED for generating light having a center wavelength of 500 nm or more and 600 nm or less. The green light has a high absorption rate due to hemoglobins in blood and suffers little influence of a disturbance light due to a sunlight, etc. Accordingly, it becomes possible to measure relatively stable blood volume pulses. As a result, for example, by being based on pulsations of the blood volume pulses by the green light, it becomes possible to obtain highly reliable heart rate and heart rate variation information.

Incidentally, oxyhemoglobins, deoxyhemoglobins (which can also be paraphrased as reduced hemoglobins), and glycated hemoglobins may have different absorption coefficients (which may be, typically, absorption spectrums) for wavelengths of red light or near-infrared light, respectively. In some embodiments, for example, the light-emitting device 15 may include a combination of a red LED having a center wavelength of 630 nm or more and 690 nm or less, and an infrared LED having a center wavelength of 810 nm or more and 990 nm or less. It is possible to obtain $SpO_2$ (which corresponds to a peripheral blood oxygen saturation level) or blood oxygen concentration or heart rate based on differences of the absorption coefficients to the above-mentioned two types of light of oxyhemoglobins and deoxidized hemoglobins.

In some embodiments, the light emitting device 15 may include, for example, a combination of different three or more (for example, three or four) LEDs for generating light beams having center wavelengths of 600 nm or more and 990 nm or less. The hemoglobin concentration in blood or the glycated hemoglobin concentration in blood, etc., may be calculated based on differences of the absorption coefficients of oxidized hemoglobins, deoxidized hemoglobins and glycated hemoglobins.

The light emitting device 15 may include a LED for generating light having a wavelength differing from the above. Since information of hemodynamic is convolved or included in the shape of the pulse wave, the blood pressure can be estimated by analyzing the shape of the blood volume pulse. In addition, the analysis of the shape of the blood volume pulse enables the estimation of the blood viscosity and the detection of the blood sugar level from the blood viscosity. The spectroscopy, for example, the near-infrared spectroscopy, the Raman spectroscopy, the infrared spectroscopy, etc., may be adapted to measure the blood sugar level. For example, the light emitting device 15 may include a combination of different two or more (for example, two or three) LEDs for generating near-infrared light beams having center wavelengths of 1,200 nm or more and 1,600 nm or less. Thereby, the blood sugar level may be calculated based on the optical absorption spectrum derived from the glucoses.

Here, there is an issue that the PPG signal acquired from the light receiving element 17 is susceptible to disturbance light in addition to performances of the light emitting element 15 and the light receiving element 17. In addition, the reflection diffusion type method is greatly affected by a disturbance (for example, external pressure) in comparison with the transmission type method. That is to say, according to the reflection diffusion type system, the blood volume pulse is measured by using the thin arteries near the epidermis of the living body. Also, for example, in the reflection diffusion type system, the absorbance of the blood volume pulse in blood is detected with regard to the distal arteries having a diameter of about 7 μm to 26 μm existing in the papillary dermis of epidermis, and to the arteries having a diameter of about 150 μm to 242 μm existing in a junction of the dermis and the subcutaneous tissues. In these terminal arteries, the volumetric change is small, and the blood flow velocity or shear velocity is reduced relatively easily due to an external pressure so that the shape of the blood volume pulse is likely to be changed. On the other hand, in the transmission type method, it is possible to measure the absorbance of hemoglobins in blood in the relatively thick arteries having a diameter of about 1 mm existing in a deep region of the subcutaneous tissues so that the volumetric change is relatively large and it may be insusceptible to an external pressure. Accordingly, it may adopt the transmission type method in order to measure the blood volume pulse more accurately based on the photoelectric method using the PPG. However, in such a case of the transmission type method, the place where it is used is restricted. That is, only parts, for example, a fingertip or an ear lobe, having a relatively high permeability may be measured according to the transmission type method.

Figure 13:
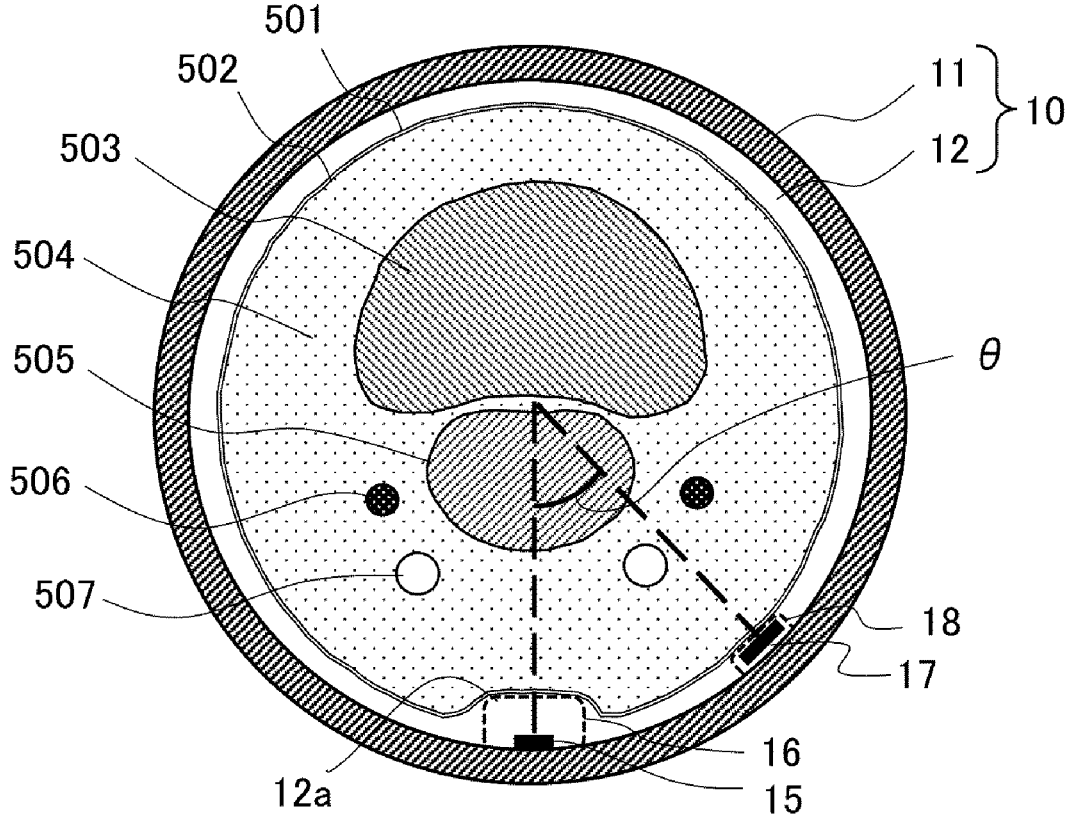
FIG. 13 is a cross-sectional view of a finger model wearing the wearable device 1 according to one embodiment.

FIG. 13 depicts a cross-sectional diagram of a human finger (i.e., a proximal nodal portion of a finger) on which the wearable device 1 according to one embodiment is attached.

Considering the above-mentioned restrictions, it would be more desirable to measure the blood volume pulse with respect to relatively thick arteries existing in a deep region of the subcutaneous fat 503 based on the reflection diffusion type method. Accordingly, in the present technology, the reflection diffusion type method and the transmission type method are partially adapted in order to detect not only the blood volume pulses at the distal arteries existing in the dermis 502 or its vicinity beneath the epidermis 501, but also the blood volume pulses at the arteries 506 by detecting light which penetrates the dermis 502 and is reflected or multiple scattered around there, by using the light receiving element 17.

At a palm side of the proximal phalange 504 of the finger root, there is the flexor tendon 505 extending along the proximal phalange 504. On both sides of the flexor tendon 505, the arterioles 506 and the nerves 507 are existed in parallel to be paired. In accordance with the examinations of the inventor, an optical simulation considering the absorbance, the scattering coefficient, and the refractive index of each the element at the epidermis 501, the dermis 502, and the subcutaneous fat 503 is conducted with respect to the finger tissues on which the wearable device 1 is attached. As a result, it is found that it is desirable to provide the light emitting element 15 on the palm side to have a directional angle of about 60° or less with regard to light emitted from the light emitting element 15, in order to irradiate more light beams in two arterioles 506 from one light source.

In a case that the outer shape of the ring body 10 is not uniform over the entire circumference of the ring, it is desirable that the light emitting element 15 is provided at a part which is intended to be disposed on the palm side. For example, the light emitting element 15 may be disposed on the opposite side of the thick portion of the ring body 10 with respect to the central axis of the ring.

The wearable device 1 may include the first optical element 16 inside the ring body 10 and the first optical element 16 is disposed to be closer to the center of the ring than the light emitting element 15. The first optical element 16 is an element which is configured to change a direction of travel of light emitted from the light emitting element 15 to a direction narrowing the directional angle of the light (in other words, a direction of travel of the light is changed to a direction in which a directional angle of the light is narrowed). By narrowing the directional angle of the light emitting element 15, it becomes possible to increase the luminous intensity of the light which is irradiated in a desired direction. As a result, a desired luminous intensity may be realized with less output. In some embodiments, the first optical element 16 is configured to have a directional angle of about 60° or less with regard to the light emitted from the light emitting element 15.

Herein the term "directional angle" is interpreted as a term meaning an index for indicating a spread of light emitted from a light source. For example, an illuminance inclined at an angle of θ from a light axis is standardized about all around the periphery, based on an illuminance (which may be a light flux or a light intensity) on a brightest light axis. Then, the directional angle is obtained as a value by doubling the angle θ which forms an angle of one half of the illuminance. It is possible to calculate the directional angle, for example, by measuring the illuminance while relatively rotating the light receiving element centering around the light emitting element.

Figure 5:
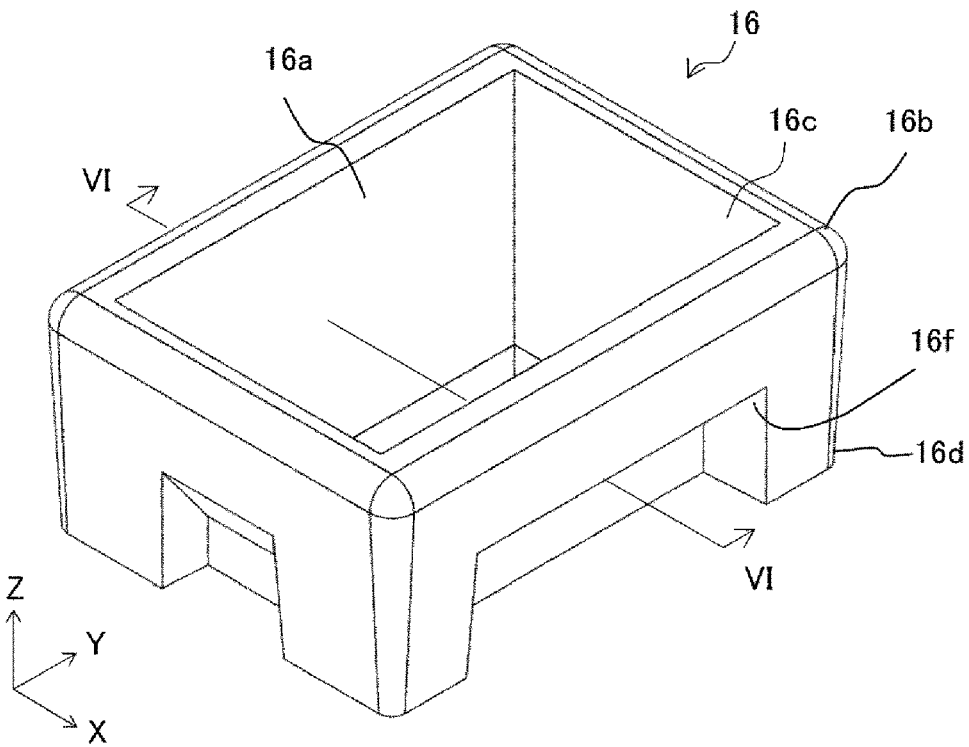
FIG. 5 is a perspective view of the first optical element 16 according to one embodiment.
Figure 6:
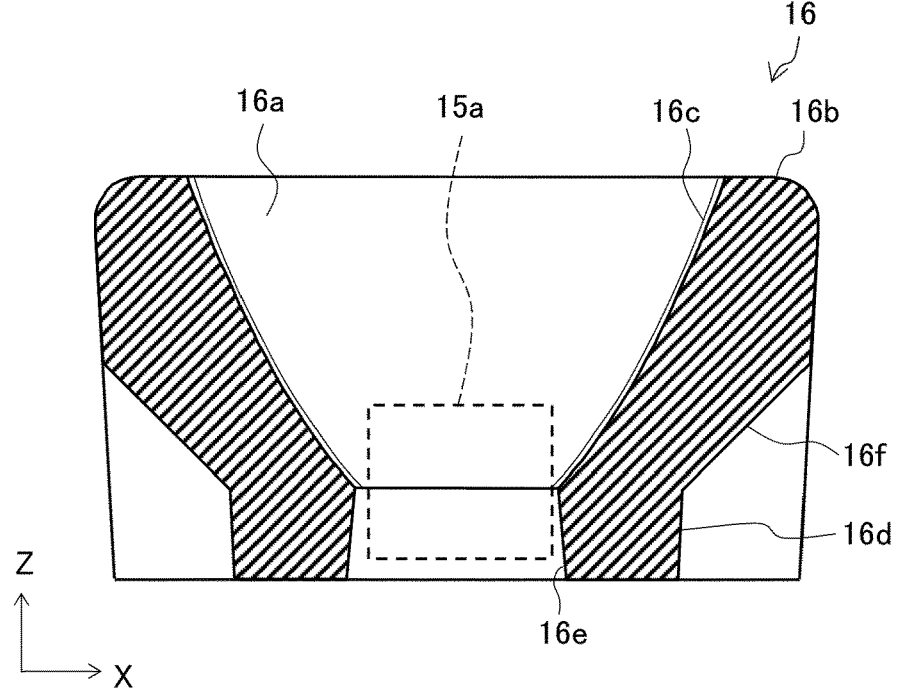
FIG. 6 is a cross-sectional view along line VI-VI in FIG. 5.

FIG. 5 depicts a perspective view of the first optical element 16 according to one embodiment, and FIG. 6 depicts a cross-sectional view taken along line VI-VI in FIG. 5. By providing the first optical element 16, it becomes possible to efficiently irradiate the light which is emitted from the light emitting element 15 to the arterioles 506 at a higher light intensity. Therefore, it becomes possible to increase the detection accuracy of the blood volume pulse.

Figure 9:
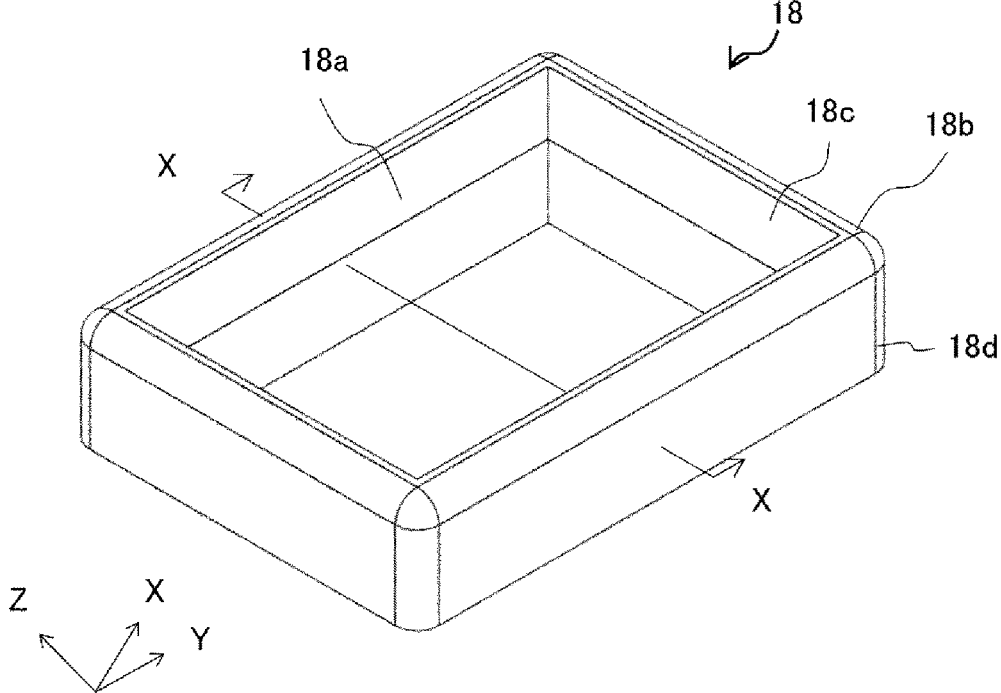
FIG. 9 is a perspective view of the second optical element 18 according to one embodiment.
Figure 10:
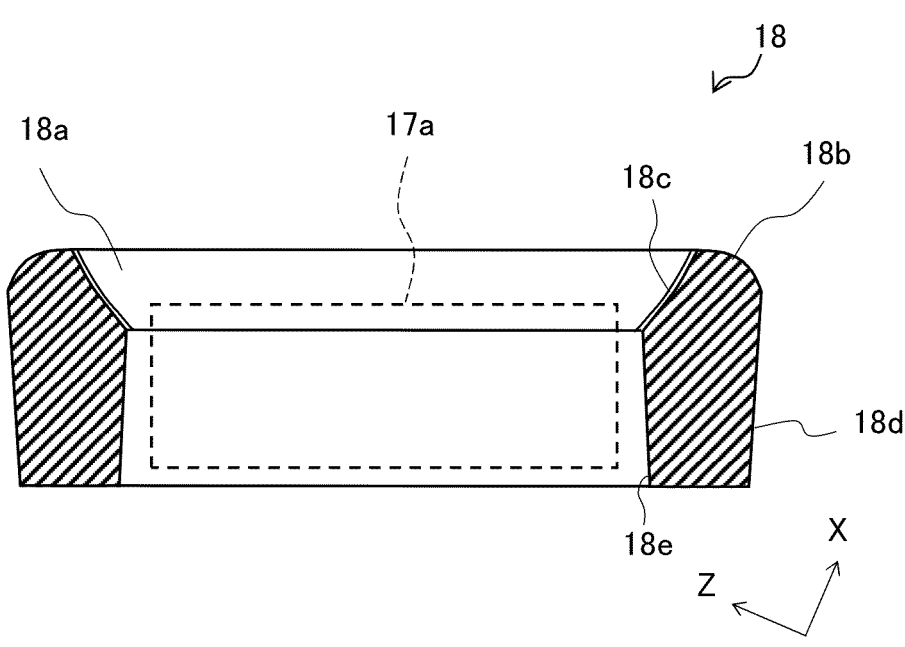
FIG. 10 is a cross-sectional view along line X-X in FIG. 9.

In addition, the wearable device 1 may include the second optical element 18 inside the ring body 10 and the second optical element 18 is disposed to be closer to the center of the ring than the light receiving element 17. The second optical element 18 is an element for changing a traveling direction of light (which is emitted from the light emitting element 15) toward the light receiving element 17. FIG. 9 depicts a perspective view of the second optical element 18 according to one embodiment, and FIG. 10 depicts a cross-sectional view taken along line X-X in FIG. 9. The second optical element 18 is provided with regard to the light which reaches at a vicinity of the light receiving element 17 after passing through biological tissues and being reflected and/or scattered back. Accordingly, it becomes possible to irradiate more light (i.e. at a higher light intensity) to the light receiving element 17. As a result, it becomes possible to increase the detection accuracy of the blood volume pulse.

Hereinafter, the first optical element 16 and the second optical element 18 may be collectively referred as the "optical elements 16, 18" in a case that the first optical element 16 and the second optical element 18 may not be distinguished from one another.

It is desirable that the optical elements 16, 18 have reflective surfaces 16a, 18a which are configured to be gradually separated from radius lines connecting the center of the ring and the light emitting element 15 and the light receiving element 17, as progressing to the inner peripheral surface (or the center of the ring) from the light emitting element 15 and the light receiving element 17, respectively. In a case that the first optical element 16 is provided with the above-mentioned reflective surfaces 16a, it becomes possible to effectively narrow a directional angle of the light emitted from the light emitting element 15. In addition, in a case that the second optical element 18 is provided with the above-mentioned reflective surfaces 18a, it becomes possible to effectively guide the light which is irradiated to the reflective surfaces 18a toward the light receiving element 17. For example, the reflective surfaces 16a, 18a may be provided so as to surround at least parts of the light emitting element 15 and the light receiving element 17 around the radius lines. In some embodiments, the reflective surfaces 16a, 18a may be provided so as to surround the whole peripheries of the light emitting element 15 and the light receiving element 17.

In some embodiments, the optical elements 16, 18 include element bodies 16b, 18b and reflective films 16c, 18c provided thereon. The reflective surfaces 16a, 18a are constituted by the reflective films 16c, 18c. The reflective films 16c, 18c may comprise, for example, a metal film made of various kinds of metal materials. Also, the reflective films 16c, 18c may comprise, for example, a dielectric multi-layered film formed by alternately stacking high refractive index layers and low refractive index layers. In doing this, the film thickness of the dielectric multi-layered film may be designed to intensify reflected light from each boundary surface based on the interference of the light. Further, the reflective film 16c, 18c may be, for example, a combination of the metal film and the dielectric multi-layered film. The above-mentioned reflective films 16c, 18c may be formed by, for example, the physical vapor deposition (which is abbreviated to PVD) such as the sputtering, vacuum deposition, ion plating, etc.; the chemical vapor deposition (which is abbreviated to CVD) such as the thermal CVD, optical CVD, plasma CVD, epitaxial growth method, atomic layer deposition, metal organic vapor phase growth method, etc.; or the wet plating method, etc. In this case, the constituent material(s) of the element bodies 16b, 18b is not particularly limited as long as the film formations of the reflective films 16c, 18c are able to be performed.

In some embodiments, the optical elements 16, 18 may be provided with bases 16d, 18d to support the element bodies 16b, 18b thereon. The base 16d, 18d are configured not to contribute to the reflection. By using the bases 16d, 18d, it becomes possible to support the reflecting surfaces 16a, 18a to be stably located on the center side of the ring inside the light emitting element 15 and the light receiving element 17. For example, the bases 16d, 18d may be provided with through-holes 16e or 18e which are connected to the reflecting surfaces 16a, 18a and penetrate the bases 16d, 18d along the radial lines. The light emitting element 15 and the light receiving element 17 may be provided in the through-holes 16e, 18e, respectively. Accordingly, the light emitting element 15 and the light receiving element 17 may be positioned at the center side of the ring inside the reflecting surfaces 16a, 18a. In addition, the reflecting surfaces 16a, 18a may be stably positioned in relative to the light emitting element 15 and the light receiving element 17. In a case that the light emitting element 15 and the light receiving element 17 include the substrates, the optical elements 16, 18 may be mounted on the substrates, respectively.

The reflective surfaces 16a, 18a may be configured as smooth surfaces as a whole. Also, the reflective surfaces 16a, 18a may be configured to include optical surfaces having a specific lens effect or prism effect on parts thereof. Each of the reflective surfaces 16a, 18a may be, for example, any one of a flat surface, any curved surface, a hyperbolic surface, an elliptical surface, a parabolic surface, etc., or each of the reflective surface 16a or 18a may be, for example, a combination of these two or more surfaces. In some embodiments, the light emitting element 15 is arranged so as to align the optical axis of light to be generated with the radius line. In other words, the optical axis is arranged to pass through the center of the ring. In some embodiments, the light receiving element 17 is arranged so as to have a light receiving surface which is perpendicular with respect to the radius line. The center of the ring may be a center of gravity of the contours of the inner periphery which is derived from the inner peripheral surface of the ring body 10 excluding the protrusions 12a.

In some embodiments, as depicted in FIGS. 6 and 10, each of the reflective surfaces 16a, 18a of the optical elements 16, 18, for example, may have a parabolic surface. In such a case, a contour line of each cross section passing through the above-mentioned radius line becomes a parabolic line. With such a configuration, it becomes possible to guide light entering the reflecting surfaces 16a, 18a in predetermined directions.

In some embodiments, the optical elements 16, 18 include the almost rectangular parallelopiped element bodies 16b, 18b and the bases 16d, 18d. When the optical elements 16, 18 are disposed in the ring body 10, longer sides of the optical elements 16, 18 are arranged in an attitude along the central axis of the ring (which may correspond to Y-axis). The bases 16d, 18d are provided with the through-holes 16e, 18e for accommodating the light emitting element 15 and the light receiving element 17 having a chip shape or a package shape, respectively. The through-holes 16e, 18e are continuous to the cup-shaped recesses which are located in the element bodies 16b, 18b at the center side of the ring. The inner walls of the recesses become the reflecting surfaces. Each of the cross section perpendicular to the radial directions of the light emitting element 15 and the light receiving element 17 may have a rectangular frame shape. The rim of the shape may become thinner and the distance between the mutually facing reflecting surfaces 16a, 18a may become larger as approaching to the center of the ring. The reflective surfaces 16a, 18a may have an identical parabolic shape in each of the X-Z cross-section and the Y-Z cross-section.

By this configuration, the sizes of the optical elements 16, 18 along the central axis of the ring may be designed larger in accordance with the size along the central axis of the ring (width) and the curvature of the ring body 10. As a result, areas surrounded by the reflective surfaces 16a, 18a may be enlarged at the ends of the optical elements 16, 18, that face the center of the ring. Therefore, it becomes possible to enlarge an emission area of the light emitted from the optical element 16 in accordance with the ring width while narrowing a directional angle of the light emitted from the light emitting element 15. Further, it becomes possible to enlarge the light receiving areas of the optical element 18 and the light receiving element 17. As a result, it becomes possible to increase the measurement accuracy of the blood volume pulse with regard to the arteriole 506.

Figure 7:
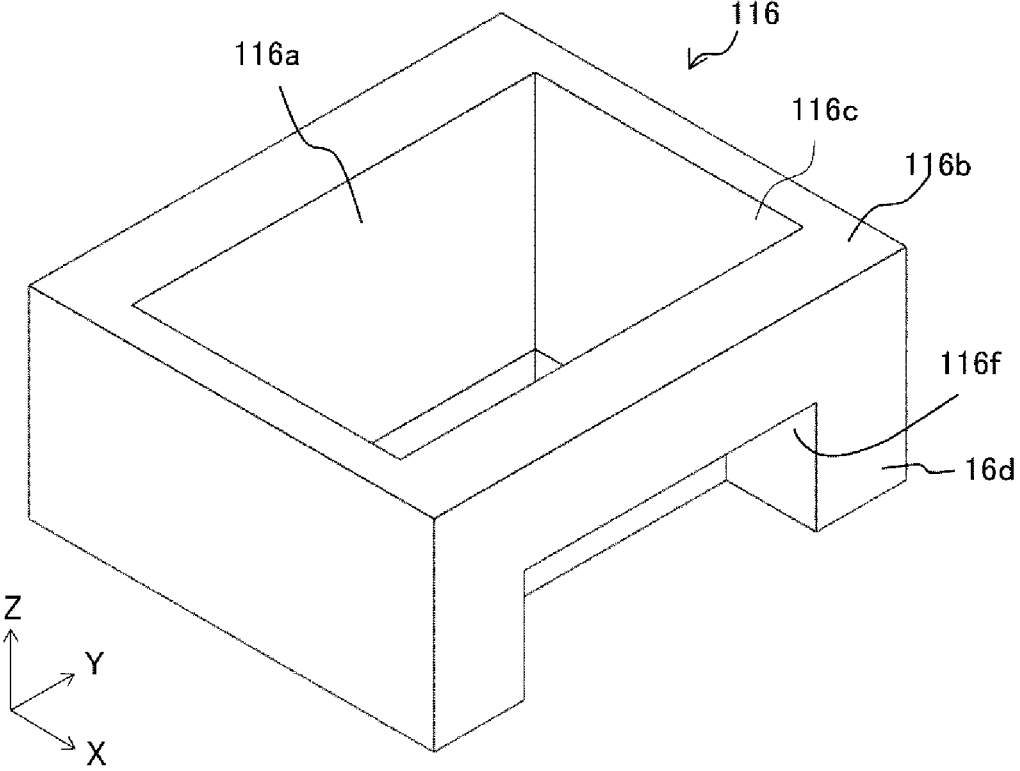
FIG. 7 is a perspective view of the first optical element according to another embodiment.
Figure 11:
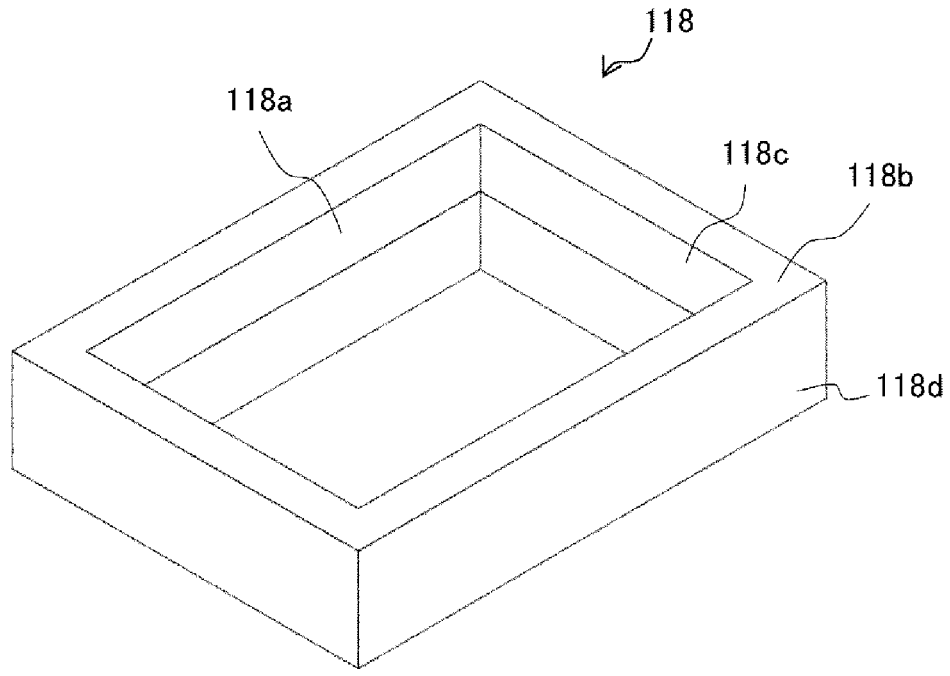
FIG. 11 is a perspective view of the second optical element according to another embodiment.

The shapes of the optical elements 16, 18 are not particularly limited other than the reflecting surfaces 16a, 18a which optically act on traveling directions of light. For example, the side surfaces of the optical elements 16, 18 may be provided with recesses 16f, 18f. The recesses 16f, 18f may be provided on all of the four sides of the optical elements 16, 18 having almost rectangular parallelepiped shapes. Also, for example, as depicted in FIG. 7, the recesses 16f, 18f may be provided on a part(s) of the four sides (for example, at two sides parallel to each other) of the optical elements 16, 18. Alternatively, for example, as depicted in FIG. 11, the recesses 16f, 18f may not be provided on the optical elements 16, 18. The corners of the optical elements 16, 18 may be chamfered. Alternatively, for example, as depicted in FIGS. 7 and 11, the corners of the optical elements 16, 18 may not be chamfered.

Figure 8:
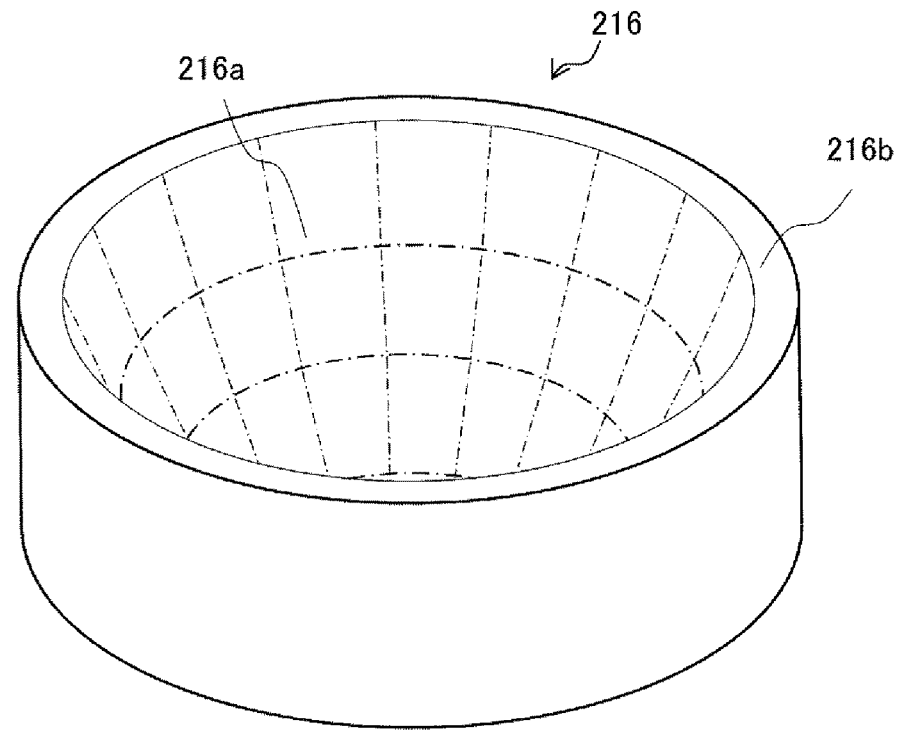
FIG. 8 is a perspective view of the first optical element according to another embodiment.

Each of the reflecting surfaces 16a, 18a of the optical elements 16, 18 may have a shape of a paraboloid of revolution around the radius line. For example, FIG. 8 depicts a perspective view of the first optical element 116 according to another embodiment. The first optical element 116 has the reflecting surface 116a which is formed to be a paraboloid of revolution around the radius line (i.e., coaxial paraboloid) so that the reflecting surface 116a is formed to have a parabolic line in all cross-sections passing through the radius line. The cross section perpendicular to the radial direction of the first optical element 116 has a circular frame shape, and the distance between the mutually facing reflecting surfaces 16a becomes larger as approaching to the center of the ring. The outer shape of the first optical element 116 is not particularly limited, for example, may be substantially cylindrical (such as an approximately cylindrical, nearly cylindrical, almost completely cylindrical, completely cylindrical). With this configuration, it is possible to suppress an occurrence of uneven intensity in the light emitted from the light emitting element 15. The reflecting surfaces 16a, 18a may have only a part of the paraboloid of revolution (non-axial paraboloid) depending on the direction of the optical axis of the light emitting device 15.

It is desirable that the reflective surfaces 16a, 18a of the optical elements 16, 18 have a sufficiently high reflectivity. In some embodiments, the reflective surfaces 16a, 18a may have a reflectivity of 70% or more. The reflectivity may be such as for example, 80% or more, such as 90% or more, such as 95% or more, or such as 99% or more. The optical elements 16, 18 may be constructed entirely of a highly reflective material. Alternatively, as described above, at least the reflective surface 16a, 18a may be constructed of a highly reflective material. The materials with high reflectivity may include various kinds of metal materials such as a gold, silver, copper, aluminum, etc. Also, the material constituting the sealing resin member 12 may include a highly refractive index material having a highly refractive index. For example, the highly refractive index material may include an optical resin material such as an acrylic resin, epoxy-based resin, highly refractive index glass, etc. Typically, the highly refractive index material may have a refractive index of 1.4 or more depending on the relationship with the constituent material of the sealing resin member 12. In some embodiments, the refractive index may be 1.5 or more. The refractive index may be such as for example, 1.6 or more, or such or 1.7 or more. Alternatively, it may be, for example, a combination of a dielectric material having a relatively high refractive index and a dielectric material having a relatively low refractive index such as $HfO_2/SiO_2$.

In a case that the ring body 10 includes the above-mentioned optical elements 16, 18 therein, the sealing resin member 12 may be provided with projections 12a at parts where the optical elements 16, 18 are disposed. For example, the protrusion 12a may be provided in a part (of the inner peripheral surface of the ring body) where the first optical element 16 is disposed, and the protrusion 12a may be formed to protrude closer to the center of the ring than another part (of the inner peripheral surface of the ring body) where the first optical element 16 is not disposed. In addition, the protrusion 12a may be provided in a part where the second optical element 18 is disposed, and the protrusion 12a may be formed to protrude closer to the center of the ring than another part where the second optical element 18 is not disposed (other than the part where the first optical element 16 is disposed).

By this configuration, at a time when the wearable device 1 is attached on a living body, the protrusions 12a are brought into close contact with the epidermis 501 of the living body to push the epidermis 501 and the biological tissues toward the center of the ring. Accordingly, it becomes possible to shorten the optical path in the body having a relatively low optical transmissivity and also to lengthen the optical path L2 in the sealing resin member 12 having a relatively high optical transmissivity. As a result, the measurement accuracy of the blood volume pulse may be increased.

In some embodiments, the optical elements 16, 18 may have ends (for example, please see "16X" in FIG. 4), that face the center of the ring, to be positioned closer to the center of the ring than the inner peripheral surface of the ring body 10. By this configuration, at a time when the protrusions 12a push the epidermis 501 of the living body toward the center of the ring, the ends (for example, please see "16X" in FIG. 4) of the optical elements 16, 18, that face the center of the ring, are also positioned closely to the center of the ring further more than the epidermis 501 which is not pushed by the protrusions 12a. Accordingly, it becomes possible to inhibit the emitted light whose raveling direction is adjusted from leaking to outside of the living body. As a result, more light beams may be propagated to a deep side of the living body. Also, it becomes possible to inhibit the propagated light traveling toward the second optical elements 18 and its circumferential part in the living body from leaking to outside of the living body. Further, it becomes possible to effectively inhibit an external light which is traveled from the outside of the living body and is not emitted from the light emitting element 15 from arriving at the second optical elements 18. As a result, the measurement accuracy of the blood volume pulse may be increased more.

As depicted in FIG. 4, as regard to the sealing resin member 12 which is configured to cover the optical elements 16, 18, the size (thickness) L3 of the sealing resin member 12 along the radius line may be thin to an extent that the durability is able to be maintained in order to position the ends which face the center of the ring, to be positioned closer to the center of the ring in the living body further more. The thickness L3 of the sealing resin member 12 covering the optical elements 16, 18 may be not more than 1 mm. For example, the thickness L3 may be not more than 0.5 mm. In some embodiments, the thickness L3 may be made in a range from about 0.2 to 0.4 mm. Also, the thickness L3 may be made in a range from about 0.2 to 0.3 mm. Incidentally, the thickness L3 of the sealing resin member 12 may be a size between (i) the end(s) (that is positioned closer to the center of the ring) of the optical elements 16, 18, and (ii) the end of the center side of the sealing resin member 12. Here, the sealing resin member 12 which is arranged at parts surrounded by the reflecting surfaces 16a, 18a of the optical elements 16, 18 is not counted in this measurement.

Also, the size of height (protruding height) L1 of the protrusion 12a along the radius line may have a height enough capable of suppressing a leakage of emitting light and suppressing an entering of outside light. Here, the first optical element 16 may be required to narrow a directional angle of light. Accordingly, the first optical element 16 having a larger height (protruding height) along the radius line may be more advantageous. Therefore, the protrusion 12a provided in a part where the first optical element 16 may be disposed has a large size of the protruding height L1. However, the protruding height L1 may be required to be limited in a range capable of giving no feeling of discomfort at the attaching of the wearable device 1 or giving no feeling of uncomfortable during performing push-in at the attaching of the wearable device 1.

From these viewpoints, the protruding height L1 may be roughly 3% or more of the inner diameter of the ring body 10. In some embodiments, the protruding height L1 may be such as for example, 4% or more, such as 5% or more, or such as 6% or more. Also, the protruding height L1 with regard to the protrusion 12a provided in a part where the first optical element 16 is disposed may be not more than roughly 10% of the inner diameter of the ring body 10. In some embodiments, the protruding height L1 may be such as for example, 9% or less, or such as 8% or less. As one example, the protruding height L1 of the protruding portion 12a provided at a part where the first optical element 16 is disposed may be 5% or more and 10% or less of the inner diameter of the ring body 10. Typically, the protruding height L1 may be in a range of from 1 mm to 2 mm. For example, the protruding height L1 may be about 1.5 mm+0.3 mm.

On the other hand, the second optical element 18 may not be required to control the directional angle of light. Accordingly, it is possible to lower the height of the second optical element 18 along the radius line compared with the height of the first optical element 16. Therefore, the protruding height L1 of the protrusion 12a provided at the part where the second optical element 18 may be disposed is smaller than the protruding height of the protrusion 12a provided at the part where the first optical element 16 is disposed. Consequently, a feeling of uncomfortable in the attaching of the wearable device 1 may be reduced. As one example, the protruding height L1 of the protruding portion 12a provided at the part where the second optical element 18 is disposed may be 3% or more and 7% or less of the inner diameter of the ring body 10. Typically, the protruding height L1 may be in a range of from 0.5 mm to 1.5 mm. For example, the protruding height L1 may be about 1 mm+0.3 mm.

Figure 12:
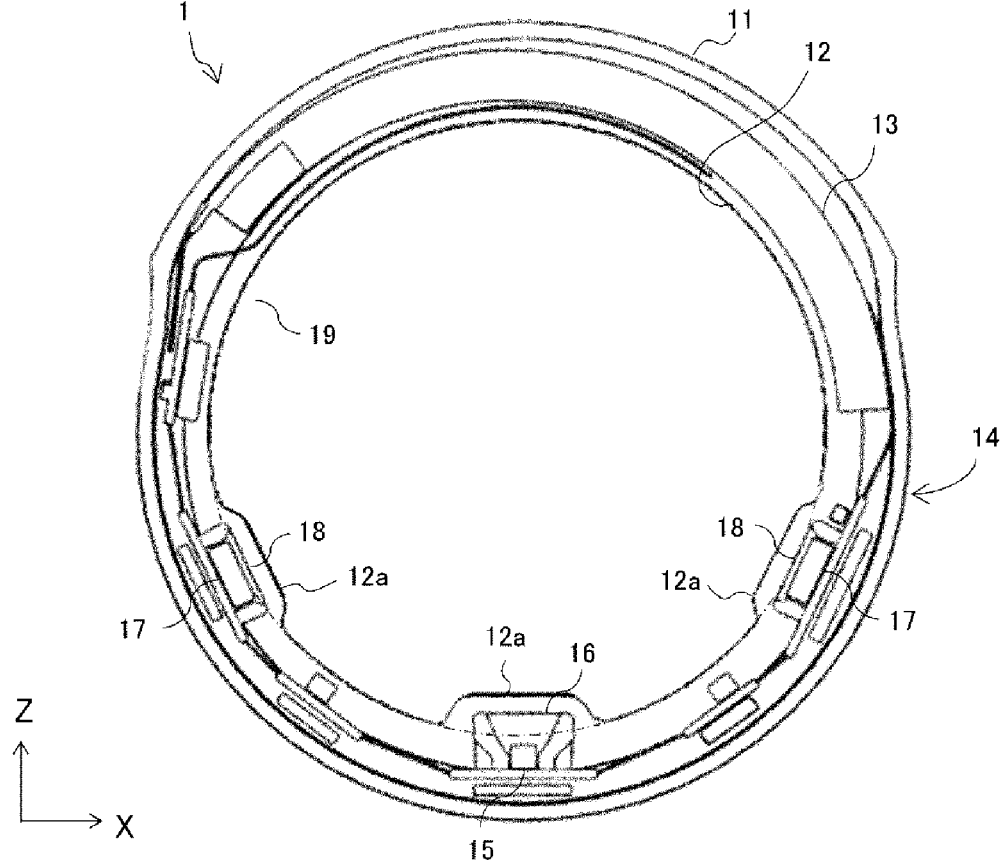
FIG. 12 is a cross-sectional view of the wearable device 1 according to another embodiment.

In a case that the protruding height L1 of the protruding portion 12a provided at the part where the second optical element 18 is disposed is lowered, it is possible to connect a part corresponding to the protruding portion 12a and a part not corresponding to the protruding portion 12a at a relatively moderate inclination (typically, with a curved surface) as depicted in FIG. 3, etc. Also, it is possible to connect a part corresponding to the protruding portion 12a and a part not corresponding to the protruding portion 12a at a relatively steep inclination (typically, with a curved surface) as depicted in FIG. 12, etc. Here, the term "relatively moderate inclination" is interpreted as a term meaning an inclination composed of a curved surface(s) having a curvature radius which is, for example, roughly, $\frac{1}{50}$ or more, more $\frac{1}{40}$ or more, and further more $\frac{1}{20}$ or more of the inner radius of the ring. By connecting a top surface of the protruding portion 12a at the part where the second optical element 18 is disposed and the inner peripheral surface of the ring body 10 by the above-mentioned relatively moderate inclination, the protruding portion 12a at the part where the second optical element 18 is disposed seems to be a non-projection shape, at a glance. By providing the relatively moderate inclination on the protruding portion(s) 12a at the part of the second optical element(s) 18, it becomes possible to further decrease a feeling of uncomfortable in the attaching of the wearable device 1. As a result, the attaching of the wearable device 1 may be improved furthermore. It is possible to design the inclination of the protruding portion 12a to exert a desired pushing effect of the protruding portion 12a (e.g. at the parts corresponding to the first optical element 16 and the second optical element 18) to the whole circumference of a finger.

It is conceivable that the thickness of the sealing resin member 12 covering the optical elements 16, 18 is increased by protruding the protrusions 12a in a hemi-spherical shape, etc. For example, it is also conceivable that a condense effect of a convex lens may be achieved by constituting the protrusions 12a with a transparent resin material having a high refractive index. However, biological tissues such as the epidermis (or skin) have a relatively high refractive index of about 1.35 to 1.4 so that a difference between the refractive index of the general optical resins and that of the biological tissues is hardly generated. As a result, when the wearable device 1 is attached on the living body, the condense effect of the convex lens by the protrusion 12*a* having a hemi-spherical shape is hardly occurred. Therefore, in the present technology, the height of the first optical element 16 may be increased and the top part of the protrusion 12*a* is made into a flat surface (or near-flat surface) along the optical elements 16, 18 (In other words, the protrusion 12*a* has a flat top surface).

As described above, the first optical element 16 provided with respect to the light emitting element 15 is configured to have an effect of narrowing the directional angle of light emitted from the light emitting element 15. It is desirable that the directional angle is reduced to about 60° or less. A directional angle of LED chip that has not been designed for collecting light is approximately is in a range of from 120° to 140°. For this reason, it is desirable that the first optical element 16 is configured to increase the directivity of light which is emitted from the light emitting element 15. For example, the directional angle may be easily decreased by increasing the size of the first optical element 16 along the radius line. In other words, the directional angle may be easily decreased by increasing the height of the reflecting surface 16*a*, As one example, the upper limit of the directing angle may be 100° or less. The upper limit of the directing angle may be such as for example, 80° or less, such as 60° or less, such as 50° or less, or such as 40° or less. However, there is a limitation in the protruding height of the protruding portion 12*a* as described above. Also, in a case that the directional angle is too narrow, for example, it may be difficult to irradiate the emitted light to the two arterioles 506 existing in the finger tissues. Therefore, as one example, the lower limit of the directing angle may be 15° or more. The lower limit of the directing angle may such as for example, 20° or more, such as 25° or more, or such as 30° or more. More specifically, for example, the surface shapes of the reflecting surface 16*a*, 18*a* may be designed to satisfy the control of the directional angle by using a general-purpose software for designing and/or analyzing of the optical system, etc.

For example, in a case that the optical axis of the light-generating element 15 is not directed to the center of the ring, the optical elements 16, 18 may be provided with a mirror, a lens, a filter, a prism, etc., so as to direct the direction of light emitted from the light emitting element 15 to the center of the ring.

Figure 19:
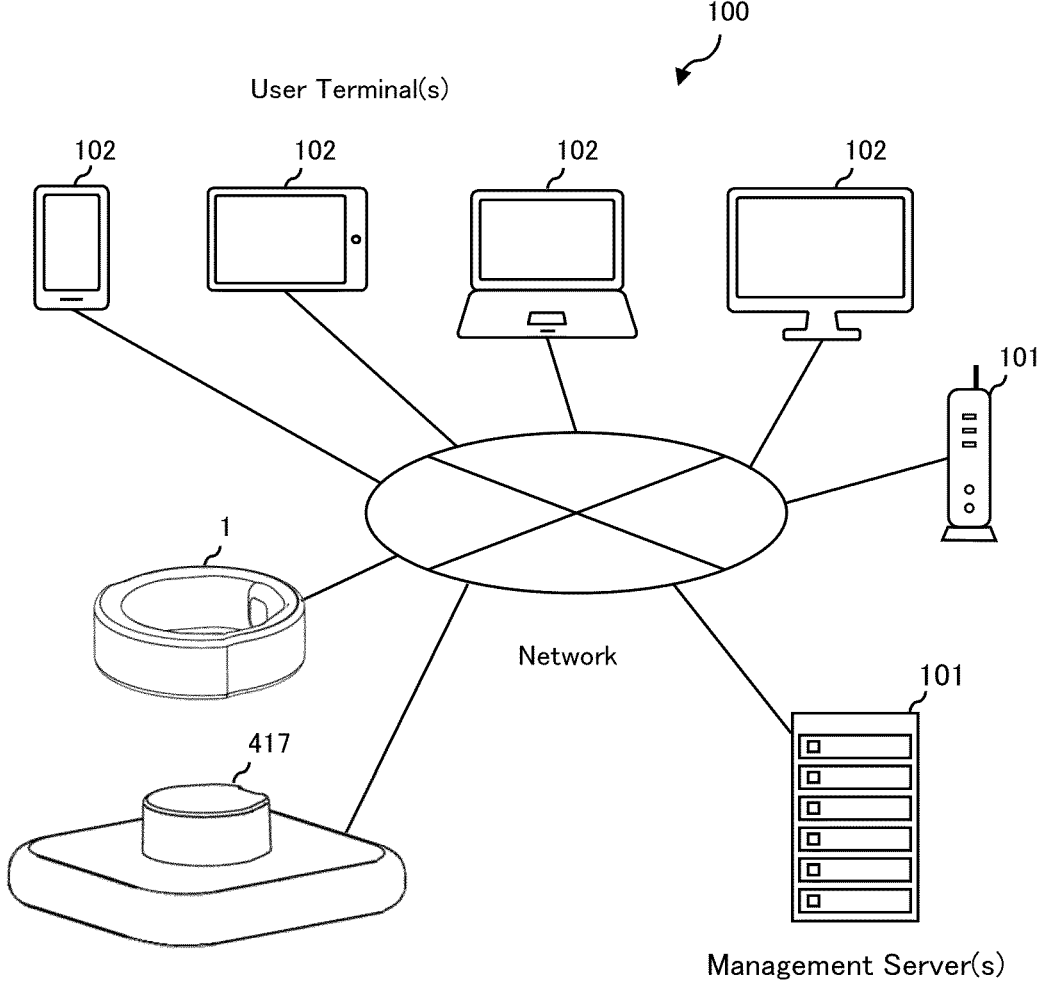
FIG. 19 depicts a configuration example of the health management system 100 according to one embodiment.
Figure 20:
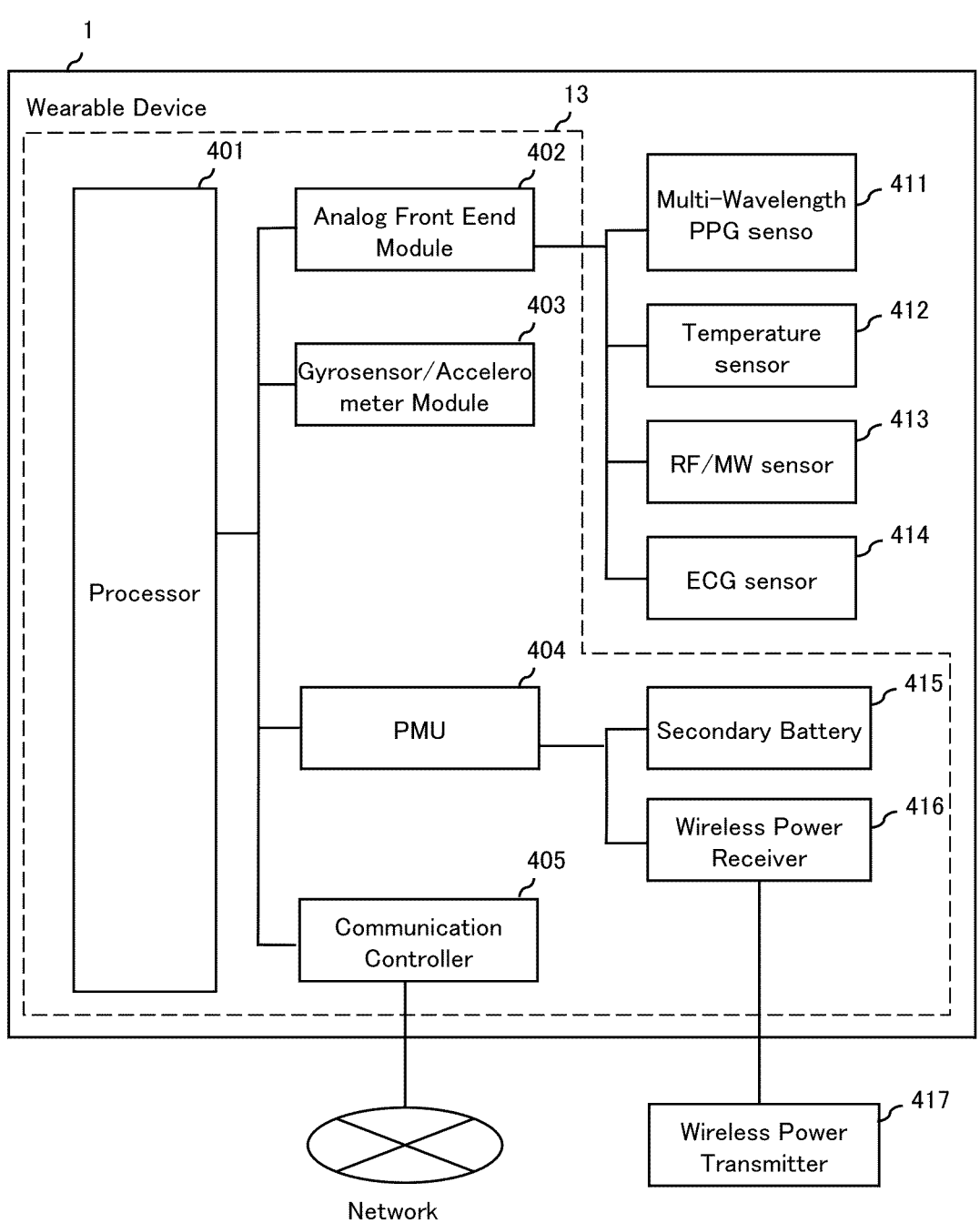
FIG. 20 depicts an example of a hardware configuration of the wearable device 1.

FIG. 20 depicts an example of a hardware configuration of the wearable device 1. In the figure, control lines and/or information lines are illustrated where an indication is thought to be necessary. However, not all control lines or information lines may not be illustrated on the product. In practice, almost all configurations may be thought to be interconnected with each other. The same applies to FIGS. 19, 21 and 22.

The electronic component 13 may include, for example, a processor 401, an analog front end 402, a gyrosensor/accelerometer module 403, a power management unit (which is hereinafter abbreviated to PMU) 404, a communication control unit 405, a secondary battery 415, a wireless power receiver 416, etc. It is possible to store these elements, for example, in a housing of the electronic component 13. Alternatively, it is also possible to mount these elements on a substrate which is prepared for the electronic component 13.

The processor 401 is configured as a digital signal processing device for controlling the operation of the analog front end 402, the gyrosensor/accelerometer module 403, the PMU 404, and the communication control unit 405. In addition, the processor 401 is configured to transmit various types of information acquired from the analog front end 402 and the gyrosensor/accelerometer module 403 to a management server(s) 101 or a user terminal(s) 102, which will be described later, via the communication control unit 405.

The analog front end 402 is configured as an analog-to-digital conversion circuit for delivering analog detection signals which are acquired from various sensors 411-414 provided in the wearable device 1 to the processor 401. As examples of the sensors, for example, a PPG sensor 411 for multi-wavelength, a temperature sensor 412, a microwave sensor 413, an electrocardiogram sensor (which is hereinafter abbreviated to ECG sensor) 414, etc., may be included. The analog front end 402 may be configured to include a processor that performs processing for removing differences between a signal of the light emitting element 15 when light is emitted and a signal of the light emitting element 15 when light is not emitted, as background.

The PPG sensor 411 for multi-wavelength, for example, is configured by using the light emitting element 15 and the light receiving element 17 according to the present technique. By using the PPG sensor 411 for multi-wavelength, the PPG signals may be detected as described above.

The temperature sensor 412 is configured for sensing temperature information, for example, with regard to a skin temperature or a body temperature at a deep part of a living body. Although the temperature sensor 412 is not especially limited thereto, but as an example, a thermopile type infrared sensor may be utilized.

The microwave sensor 413 is configured for detecting, for example, a frequency characteristic around a resonant frequency by radiating a microwave to a living body. By analyzing the frequency characteristic, it becomes possible to obtain information on the water content, the sweating quantity, the blood glucose value, etc. of the skin.

The ECG sensor 414 is configured for detecting an electrical activity associated with a movement of a heart. The ECG sensor 414 may be used as a measurement electrode according to any of various induction methods. For example, in some embodiments, the ECG sensor 414 may be configured to obtain electrocardiogram information (which is hereinafter abbreviated to ECG information) in cooperation with another ECG sensor(s) 414 provided in another wearable device(s) 1. For example, it is possible to obtain ECG information according to the bipolar induction method by using two ring-shaped wearable devices 1 which are attached on a left finger and on a right finger of a living body. It is also possible to obtain ECG information by using a combination of a ring-type wearable device 1 which is attached on a finger of one hand and a wrist-type wearable device 1 which is wound around a wrist of the other hand a living body.

The sensors 411-414 are signal detection devices (especially, sensors) for detecting, for example, various types of biological information. The other electronic element(s) 19 may be a temperature sensor 412, a microwave sensor 413, an ECG sensor 414, etc.

The gyrosensor/accelerometer module 403 is configured to include a gyro sensor and an acceleration sensor (i.e. accelerometer). The gyrosensor/accelerometer module 403 is able to detect the angular velocity and the acceleration of the wearable device 1 so that it becomes possible to obtain information on the posture, the activity, the calories burned, the number of steps, and the action determination of the living body on which the wearable device 1 is attached.

The PMU 404 is configured to control charging to a secondary battery 415 from a wireless charging system including a wireless power receiver 416 and a wireless power transmitter 417 which is an external device. The wireless charging system may be configured according to the Near Field Communication (which is abbreviated to NFC) standard in order to achieve a miniaturization and a cost-reduction of the system. Although the secondary battery 415 is not especially limited, but as an example of the secondary battery 415, the lithium polymer battery having a high energy density and a low risk of liquid leakage may be adapted.

The communication control unit 405 is configured to be connectable to another terminal(s) via a network. Each terminal is able to transmit and receive information to each other via a network regardless whether the network is wired or wireless.

The wiring circuit board 14 is configured as an element for electrically connecting the light emitting element 15, the light receiving element 17, the other electronic element 19, and the electronic component 13. The wearable device 1 may be provided with one or more wiring circuit boards 14. For example, the wiring circuit board 14 may be a flexible printed circuit (which is abbreviated to FPC) in which a wiring member is printed on a flexible board. Almost any electronic element may be mounted on the wiring circuit board 14.

Figure 17:
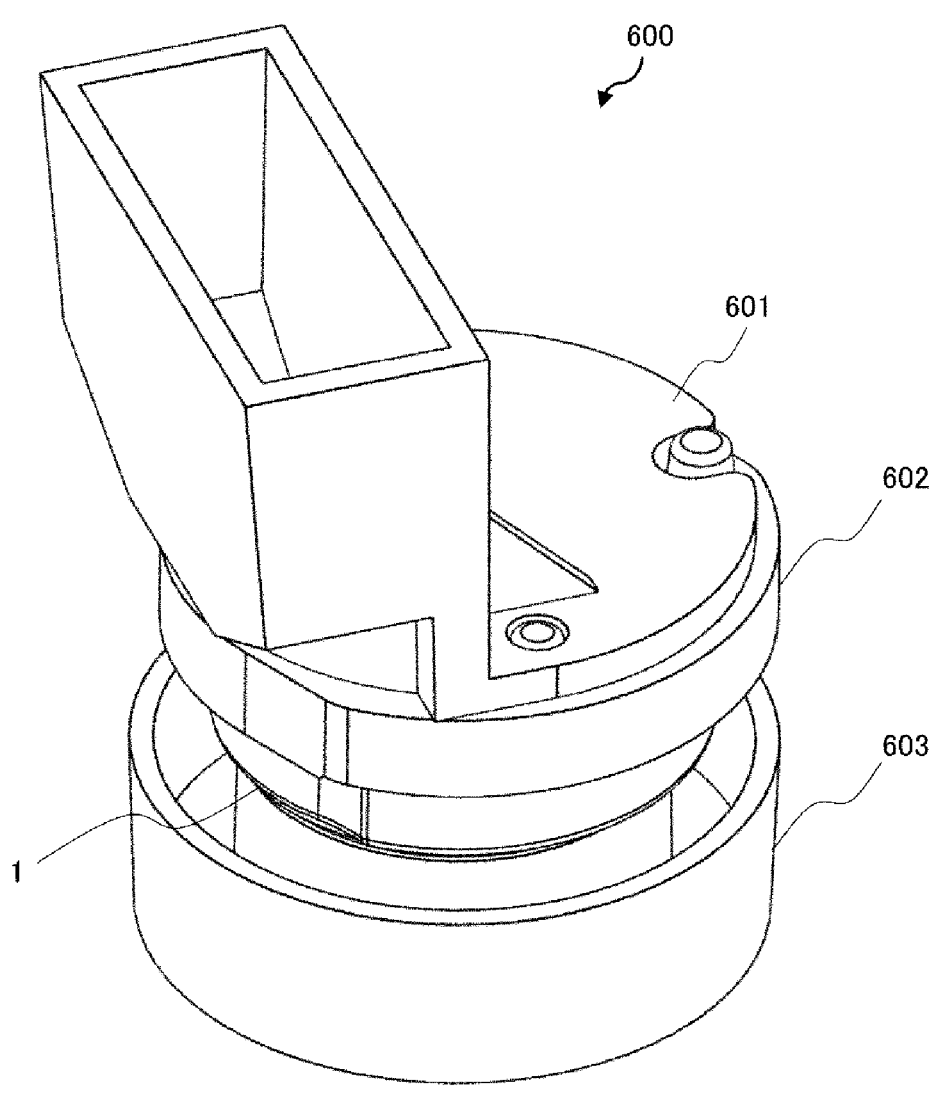
FIG. 17 is a perspective view of a jig 600 for manufacturing the wearable device 1 according to one embodiment.
Figure 18:
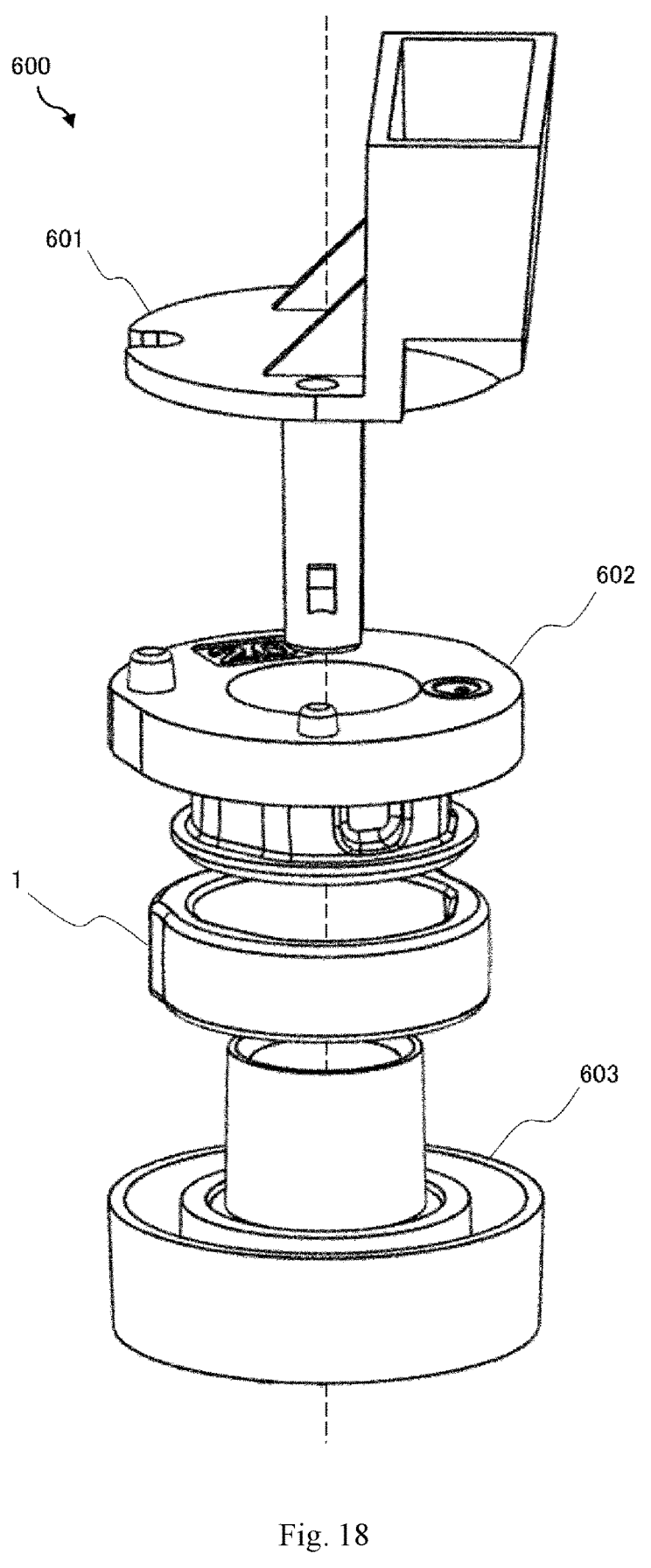

Although the wearable device 1 is not especially limited, but as an example of the wearable device 1, it may be suitably manufactured by the resin casting utilizing a jig 600 as depicted in FIGS. 17 and 18. The jig 600 is composed of an upper mold 601, a silicone core mold 602, and a lower mold 603. During the course of the manufacturing of the wearable device 1, the light emitting element 15, the light receiving element 17, the other electronic element 19, and the electronic component 13 which are connected by the wiring circuit board 14 and the optical elements 16 and 18 may be assembled in the recessed part 11a of the exterior member 11 which is prepared in advance. The optical elements 16 and 18 may be assembled with the light emitting element 15 and the light receiving element 17 in advance. The light emitting element 15, the light receiving element 17, the other electronic element 19, the electronic component 13 and the wiring circuit board 14 may be positioned in the recessed part 11a of the exterior member 11 and fixed therein by using a suitable method such as a double-sided tape, adhesive, fixing means (for example, any fixing structure), etc. Also, the light emitting element 15, the light receiving element 17, the other electronic element 19, and the board part of the wiring circuit board 14 may be stored in the recessed part 11a of the exterior member 11 so as not to project from the exterior member 11 to outside. In this way, it is possible to suppress a position deviation of these elements in the subsequent resin casting step.

The elements are arranged in the exterior member 11 by this manner, then the silicone core mold 602 is mounted to the exterior member 11. The silicone core mold 602 is a mold for molding the inner peripheral surface of the sealing resin member 12. As a result, a cavity is formed between the exterior member 11 and the silicone core mold 602.

Subsequently, the exterior member 11 and the silicone core mold 602 in the mounted state are fixed by using the upper mold 601 and the lower mold 603 (c.f. FIG. 17). The silicone core mold 602 is provided with an injection hole, for example, for injecting a resin material on an upper surface. In addition, the upper mold 601 is provided with a flow path (which may be a spool) continuous to the injection hole.

Subsequently, a resin material in a flowing state prepared for the sealing resin member 12 is injected from the injection molder (not shown) to the cavity through the upper mold 601. In some embodiments, for example, as a base polymer, a liquid resin material containing a bisphenol A type epoxy resin is injected with a polymerization initiator at room temperature (for example, at 25° C.). The resin material is thereafter cured by being heated to a temperature of about 60° C. Consequently, the sealing resin member 12 may be integrally formed in a predetermined shape with respect to the exterior member 11.

After curing of the sealing resin member 12, the upper mold 601 and the lower mold 603 are opened, and then the silicone core mold 602 is deformed to release the results. As a result, the wearable device 1 may be obtained. However, the manufacturing method of the wearable device 1 is not limited to this example. In addition, the wearable device 1 may be coated for decoration as needed.

System and Method for Health Management

FIG. 19 depicts an example of a configuration of a system for managing health of user (which is hereinafter abbreviated to health management system) 100 according to one embodiment. The health management system 100 and a method for managing health (which is hereinafter abbreviated to health management method) in accordance with the present technology are configured as a system and a method for monitoring biological information and managing health by using the wearable device 1. The health management system 100 includes the one or more wearable device(s) 1, the one or more management server(s) 101, and the one or more user terminal(s) 102. The health management system 100 may additionally include the one or more wireless power transmitter(s) 417.

The management server 101 and the user terminal 102 are configured to be able to transmit and receive information to each other, for example, via a network. Also, the wearable device 1 and the user terminal 102 are configured to be connectable to each other by using a wireless communication system such as the Bluetooth (registered trademark). However, the wearable device(s) 1, the management server(s) 101, the user terminal(s) 102, and the wireless power transmitter(s) 417 may be configured to transmit and receive information to and from each other, for example, via a network. Further, any two or more of the management server 101, the user terminal 102, and the wireless power transmitter 417 may be integrally configured. Also, any one of the management server 101, the user terminal 102, and the wireless power transmitter 417 may be configured to be separated into two or more units.

Each terminal of the health management system 100 (for example, the management server 101 and the user terminal 102) may be, for example, a mobile terminal such as a smart phone, tablet, mobile phone, mobile information terminal (for example, personal digital assistant which is abbreviated to PDA); or each terminal of the health management system 100 may be, for example, a stationary computer, a portable computer or a server located on a cloud or network. From the point of function, each terminal may be configured as a virtual reality (which is abbreviated to VR) terminal, an augmented reality (which is abbreviated to AR) terminal, or a mixed reality (which is abbreviated to MR) terminal, etc. Alternatively, it may be a combination of these terminals. For example, a combination of one smartphone and one wearable terminal may logically function as one terminal. Further, it is possible to use another type of information processing terminal other than these.

Each terminal of the health management system 100 includes a processor for executing an operating system, an application, a program, etc.; a main storage such as the Random Access Memory (which is abbreviated to RAM), etc.; an auxiliary storage such as the IC card, hard disk drive, Solid State Drive (which is abbreviated to SSD), a flash memory, etc.; a communication control unit such as the network card, wireless communication module, mobile communication module, etc.; an input device such as the touch panel, keyboard, mouse, voice input device, movement detection input device using images which are captured from camera unit, etc.; and an output device such as the monitor, display, speaker, oscillator, etc. In addition, the output device may be a device or a terminal for transmitting information for outputting to an external monitor, a display, a printer, a device, etc.

The main storage is capable of storing various programs and applications (including software modules) etc., therein. When the processor executes the program or the application, each functional element of the entire system is realized. Each module may be an independent program or application, or each module may be implemented as a form of subprograms or functions in a part of an integrated program or application. Also, each module may be implemented as a hardware (or a hardware module), for example, by integrating circuits or employing a microcomputer. In addition, each module may be provided in a single terminal, or each module may be provided by being separated into two or more terminals which are connected to each other via a network.

In this specification, each module is described as the subject of an action (or the subject of the sentence) which performs the processings, but practically a processor which is configured to process various programs and applications (including modules) performs the processings.

The auxiliary storage is capable of storing various databases (DB) etc., therein. Here, the term "database" is interpreted as a term meaning a data set that is organized and/or collected to accommodate to any data manipulation (for example, extraction, addition, deletions, overrides, etc., of any data) from the processor or the external computer. The auxiliary storage is a functional element (or a storage device) that stores one or more of data sets. The method of implementing the database is not particularly limited. For example, it is possible to use a database management system, a spreadsheet software, or a text file such as the XML, JSON, etc., for implementing the database.

Figure 21:
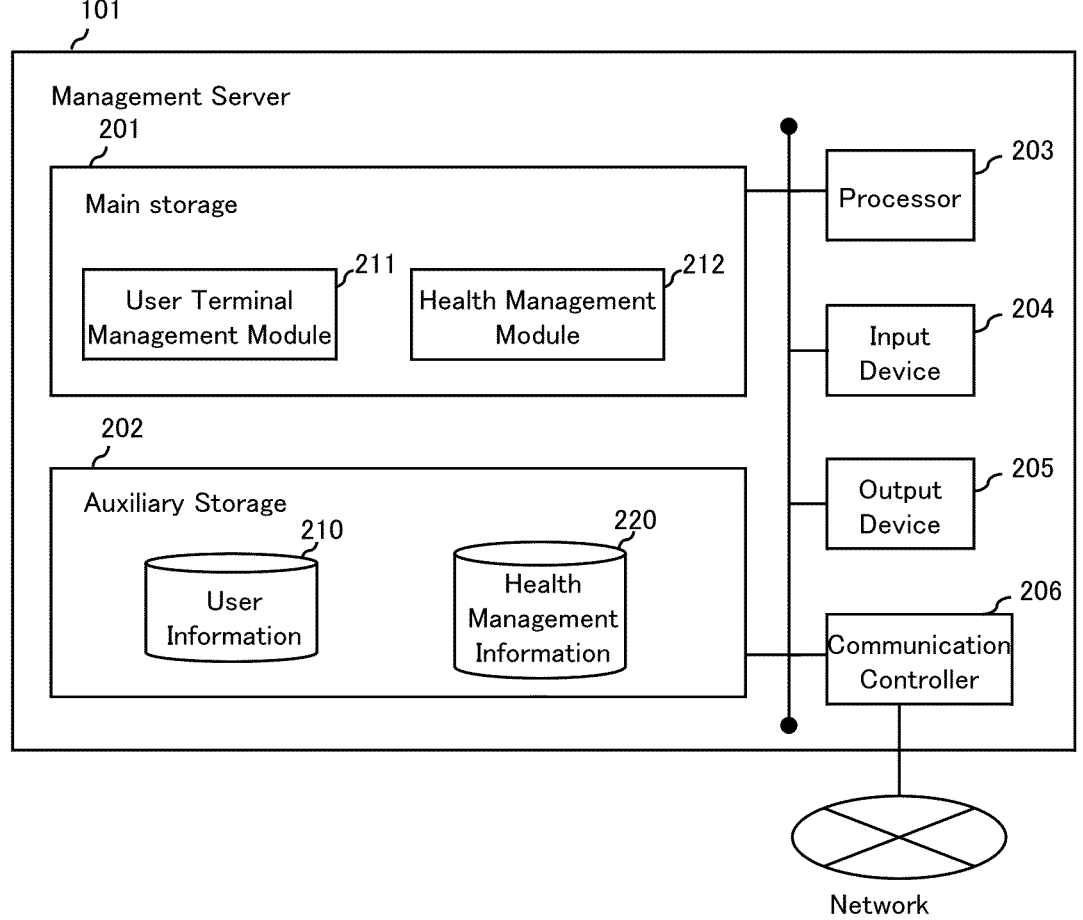
FIG. 21 depicts an example of a hardware configuration of the management server 101.

FIG. 21 depicts an example of a hardware configuration of the management server 101.

The management server 101 is configured as an element for managing the health management system 100 of the present embodiment. For example, the management server 101 may be configured by using a server which is located on a cloud. The management server 101 is provided with a main storage 201 and an auxiliary storage 202. In addition, the management server 101 is provided with a processor 203, an input device 204, an output device 205 (as an example of output means), and a communication control unit 206, as described above.

The main storage 201 is capable of storing programs and applications (for example, a user terminal management module 211 and a health management module 212) therein. When the processor 203 executes the program or the application stored in the main memory 201, each functional element of the management server 101 is realized.

The auxiliary storage 202 is capable of storing information which is necessary for operating the health management system 100. For example, the auxiliary storage 202 stores the user information 210, the health management information 220, etc., therein.

The user terminal management module 211 is configured to manage the operation of the user terminal 102. For example, the user terminal management module 211 controls, in conjunction with the user execution module 311 of the user terminal 102, the basic operations of the health management application which is executed in the user terminal 102. For example, the user terminal management module 211 acquires registration information of a user who utilizes the health management application. Then, the user terminal management module 211 outputs (for example, stores) the registration information to the user information 210 in the auxiliary storage 202 and manages it.

The health management module 212 is configured to manage information regarding the health of the user. Specifically, the health management module 212 acquires, for example, biomedical information acquired by the wearable device 1, from the user terminal 102, in cooperation with the user health management module 312 of the user terminal 102. In addition, the health management module 212 is able to calculate health management information which is at least one of the heart rate, the blood oxygen saturation level, the blood pressure, and the blood sugar level, according to the PPG method, based on the acquired biometric information. The health management module 212 may be configured to calculate the posture or the activity of the user, the calories burned, the number of steps, the action determination, the body temperature (which may be the skin temperature or the body temperature at a deep part of the subject), the moisture content of skin, the perspiration, the blood sugar level, the ECG, or other health management information, based on the acquired biometric information. The health management information may include a management index for preventing disease which is defined according to the need such as the vessel health index, activity status, levels of stress, levels of depression, lifestyle-related disease, etc. The health management module 212 outputs (for example, stores) the calculated health management information to the health management information 220 in the auxiliary storage 202 and manages it.

In addition, the health management module 212 outputs (for example, displays) the calculated health management information to a display (which is an example of the output device 305) of the user terminal 102, for example, in cooperation with the user health management module 312 of the user terminal 102.

In addition, the health management module 212 may be provided with a configuration for notifying a result when a predetermined feature is observed in the calculated health management information. The notifying method is not particularly limited. For example, it is possible to display it on a display of the user terminal 102, or to transmit it as an e-mail or a message to a predetermined destination.

Figure 22:
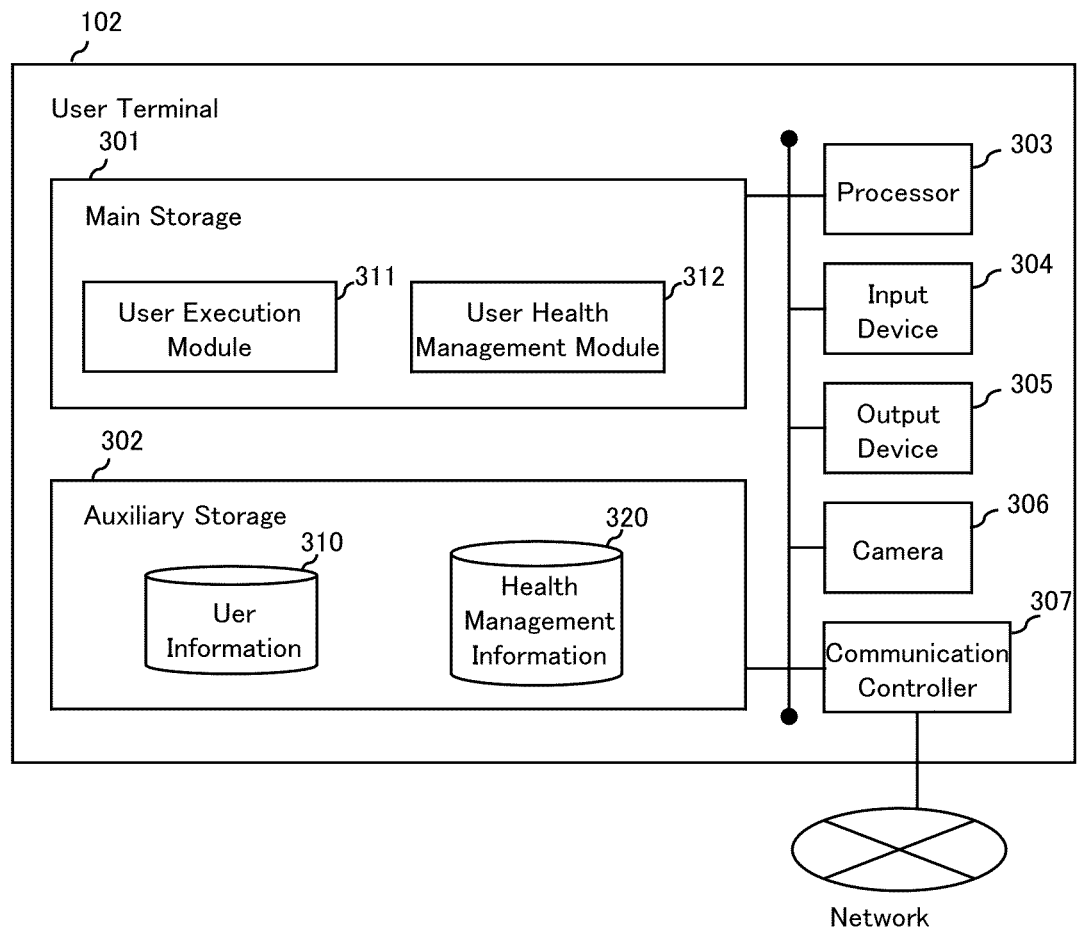
FIG. 22 depicts an example of a hardware configuration of the user terminal 102.

FIG. 22 depicts an example of a hardware configuration of the user terminal 102.

The user terminal 102 is a terminal which may be operated by a user utilizing the health management system. For example, the user terminal 102 may be constituting of a terminal such as the smartphone, tablet, notebook type PC ("PC" is an abbreviation of "personal computer"), a desktop type PC, etc. The user terminal 102 is provided with a main storage 301 and an auxiliary storage 302. In addition, the user terminal 102 is provided with a processor 303, an input device 304, an output device 305, a camera 306, and a communication control unit 307, as described above.

The main storage 301 is capable of storing programs and applications (for example, a user execution module 311 and a user health management module 312) therein. When the processor 303 executes the program or the application, each functional element of the user terminal 102 is realized.

The auxiliary storage 302 is capable of storing information which is necessary for operating the health management system 100. For example, the auxiliary storage 202 stores the user information 310, the health management information 320, etc., therein. The user information 310 and the health management information 320 may be partly or entirely the same as the user information 210 and the health management information 220.

The user execution module 311 is configured to control basic operations of the user terminal 102. For example, the user execution module 311 is able to receive information of user relation inputted from the user himself/herself and output (for example, store) it to the user information 310 in the auxiliary storage 302. In addition, the user execution module 311 is able to control, in cooperation with the user terminal management module 211 of the management server 101, for example, basic operations of health management which are executed by using the health management system 100. The user execution module 311 is able to transmit the user information to the management server 101 through, for example, the communication control unit 206.

The user health management module 312 is configured to control basic operations of the wearable device 1, in conjunction with the processor 401 of the wearable device 1. The user health management module 312 is connected to the wearable device 1 through, for example, the communication control unit 206, using a short-range wireless communication such as the Bluetooth (registered trademark). For example, the user health management module 312 is able to acquire the biometric information which is obtained from each of sensors 411 to 414 of the wearable device 1 and output (for example, store) it to the health management information 320 in the auxiliary storage 302.

The user health management module 312 is able to transmit the biometric information acquired from the wearable device 1 to the management server 101 in cooperation with the user health management module 312 of the management server 101. Further, the user health management module 312 is able to acquire the health management information of the user which is calculated by the management server 101, in cooperation with the user health management module 312 of the management server 101, and output (for example, display) it to the user terminal 102.

In accordance with the method for managing health of the present technology, for example, the user may obtain various health management information by utilizing the above-mentioned wearable device 1. During the course of the method for managing health, firstly, a user puts (which can also be paraphrased as "attaches", "wears" and other similar variations) the wearable device 1 on himself/herself to acquire biological information. Secondly, based on the biological information obtained by putting the wearable device 1 on the living body, health management information which is at least one of the heart rate, the blood oxygen saturation level, the blood pressure, and the blood glucose value is calculated according to the PPG method. Subsequently, the calculated health management information is outputted to, for example, a display such as the smartphone's display, PC's display, etc.

The wearable device 1 according to the present technology is configured to be capable of detecting the blood volume pulses from the arterioles existing in the deep region of the living body so that high-precision health management information may be obtained non-invasively. In addition, the wearable device 1 is configured as a small and light device, for example, as a ring type device so that the biometric information may be obtained without giving excessive load to the user physically and actively. Furthermore, the wearable device 1 is configured to include the optical elements 16, 18 to increase the output density of the light-emitting element 15 and efficiently obtain the blood volume pulses from the arterioles existing in the deep region of the living body while suppressing the power consumption of the device. Especially, the wearable device 1 may be used for a long time with a single charge. For example, the user may acquire information regarding to the bioactivity lasting for 24 hours (or about one day), without perceiving discomfort or burden, and use it for health management.

EXAMPLE

The structure of the ring type wearable device 1 is examined and evaluated by using an optical simulation system based on a finger model. During the course of the optical simulation, the optical simulation tool, "Trace Pro" (which is available from Lambda Research Corporation Co. in the United States) is used.

FIG. 13 depicts a cross-sectional view of a finger model equipped with the wearable device 1 which is prepared for the optical simulation. The finger model is designed to include the ring body 10 (which includes the exterior member 11 and the sealing resin member 12) of the wearable device 1, the light emitting element (which includes the LED) 15 in a form of a package, the first optical element 16, the light receiving element 17 in a form of a chip, the second optical element 18; and also the epidermis 501, the dermis 502, the subcutaneous fat 503, the proximal phalange 504, the flexor tendon 505, the arterioles 506, and the nerves 507 existing in the finger. In this finger model, some finger tissues are assumed to be in a situation of being pressurized by the sealing resin member 12 of the wearable device 1. Therefore, some finger tissues are assumed to be deformed into a shape parallel with the sealing resin member 12. For example, the following values are adopted as optical coefficients, etc., with regard to each of the living body's elements, in accordance with the model.

TABLE 1

| | LIGHT SOURCE WAVELENGTH [nm] | ABSORPTION COEFFICIENT m_a [mm$^{-1}$] | SCATTERING COEFFICIENT m_s [mm$^{-1}$] | REFRACTIVE INDEX n [—] | ANISOTROPIC SCATTERING COEFFICIENT g [—] | REFLECTIVITY [—] | TRANSMISSIVITY [—] |
|---|---|---|---|---|---|---|---|
| EPIDERMIS | 940 | 0.03 | 12.3 | 1.42 | 0.89 | 0.32 | 0.68 |
| DERMIS | 940 | 0.03 | 7 | 1.38 | 0.91 | 0.26 | 0.74 |
| SUBCUTANEOUS FAT | 940 | 0.03 | 7 | 1.38 | 0.91 | 0.26 | 0.74 |
| PROXIMAL PHALANGE | 940 | 0.02 | 26.1 | 1.4 | 0.94 | 0.47 | 0.53 |

TABLE 1-continued

| | LIGHT SOURCE WAVELENGTH [nm] | ABSORPTION COEFFICIENT m_a [mm⁻¹] | SCATTERING COEFFICIENT m_s [mm⁻¹] | REFRACTIVE INDEX n [—] | ANISOTROPIC SCATTERING COEFFICIENT g [—] | REFLECTIVITY [—] | TRANSMISSIVITY [—] |
|---|---|---|---|---|---|---|---|
| FLEXOR TENDON | 940 | 0.03 | 7 | 1.38 | 0.91 | 0.26 | 0.74 |
| ARTERIOLE (SaO₂ 97%) | 940 | 0.64 | 65 | 1.36 | 0.99 | 0.53 | 0.47 |
| NERVE | 940 | 0.03 | 7 | 1.38 | 0.91 | 0.26 | 0.74 |

The wearable device 1 is configured to include two light receiving elements 17 and one light emitting element 15, and the two light receiving elements 17 are arranged to be paired on both sides of the one light emitting element 15. It is assumed that the angle formed between the line going through the center of the ring and the light emitting element 15 and the line going through the center of the ring and the light receiving element 17 is expressed as θ, and the angle θ is gradually changed by 10° in a range of from 30° to 110°. As the light emitting element 15A, the LED having a wavelength of 940 nm, a directional angle of 120°, an emission area of a square of 0.28 mm (i.e. 0.28 mm×0.28 mm), and an emission intensity of 1 mW is used. The light receiving surface of the light receiving element 17 is made into a flat surface having an area of a square of 1.5 mm (i.e. 1.5 mm×1.5 mm).

Figure 16:
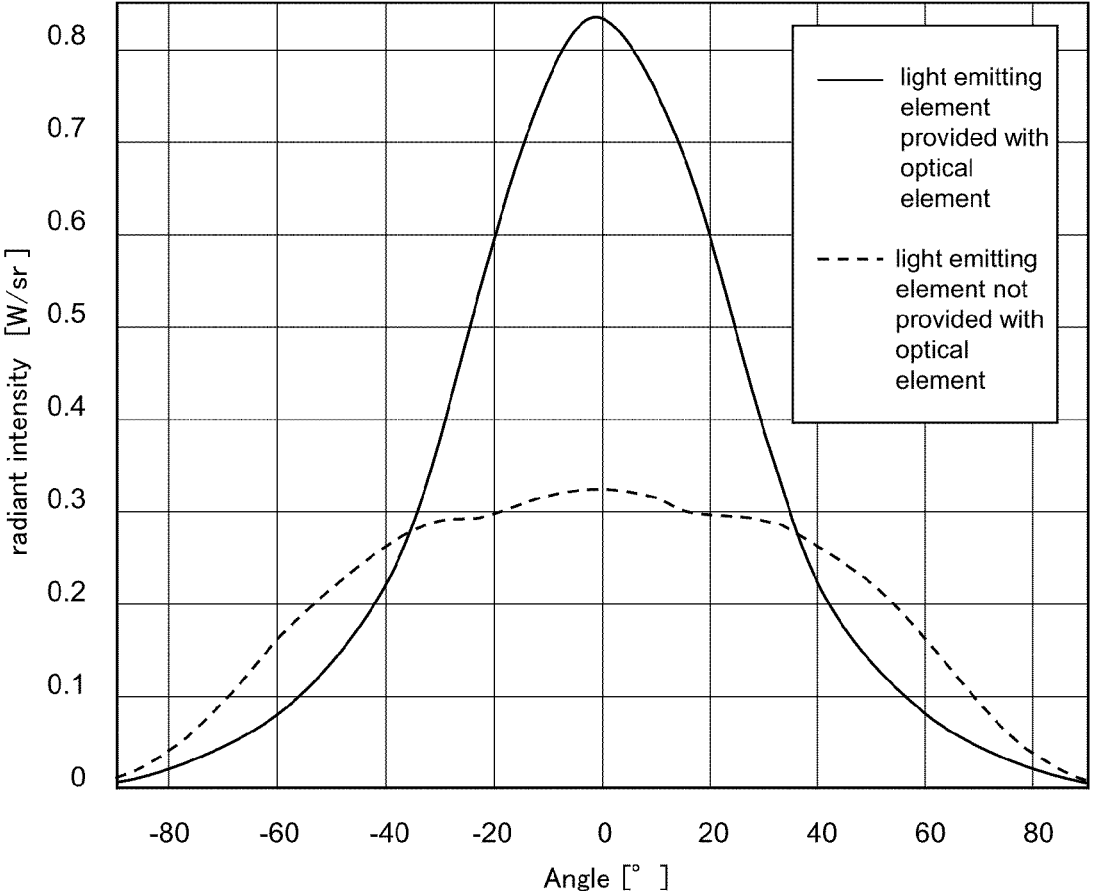
FIG. 16 depicts radiation intensity distributions of the light emitting element, depending on the presence or absence of the optical elements.

During the course of the simulation, the research is made to both of (i) a model which is not provided with the optical elements 16 and 18 and (ii) a model which is provided with at least one of the first optical element 16 and the second optical element 18. The first optical element 16 is configured to have the shape depicted in FIGS. 5 and 6 and the second optical element 18 is configured to have the shape depicted in FIGS. 9 and 10. Each of the optical elements 16, 18 is configured to have the element body 16b, 18b made of a resin material and the reflective surface 16a, 18a consisting of an aluminum evaporated film (which has a reflectivity of 90%) on the element body 16b, 18b. The first optical element 16 is provided with the reflective surface 16a so as to suppress the directional angle of the above-mentioned light emitting element 15 to an angle of 58°. FIG. 16 depicts two types of radiation intensity distributions from the light emitting element 15. Here, in one case, the first optical element 16 is provided, and in another case, the first optical element 16 is not provided.

The optical elements 16, 18 are configured to have ends (for example, please see "16X" in FIG. 4), that face the substantially center of the ring, to be positioned closer to the substantially center of the ring than the inner peripheral surface of the sealing resin member 12. The thickness (L2) of the sealing resin member 12 covering the optical element 16, 18 is made to have a length of 0.46 mm. The protruding height (L1) of the protrusion 12a corresponding to a part of the first optical element 16 is made to have a length of 1.38 mm. The length (L3) from a surface of the light emitting element 15 at the center side of the ring to a surface of the sealing resin member 12 is made to have a length of 1.48 mm. Also, the length (L5) of an opening (which correspond to opposing reflecting surfaces 16a) at the end of the first optical element 16 at the center side of the ring along the X direction is made to have a length of 2.39 mm.

Figure 14:
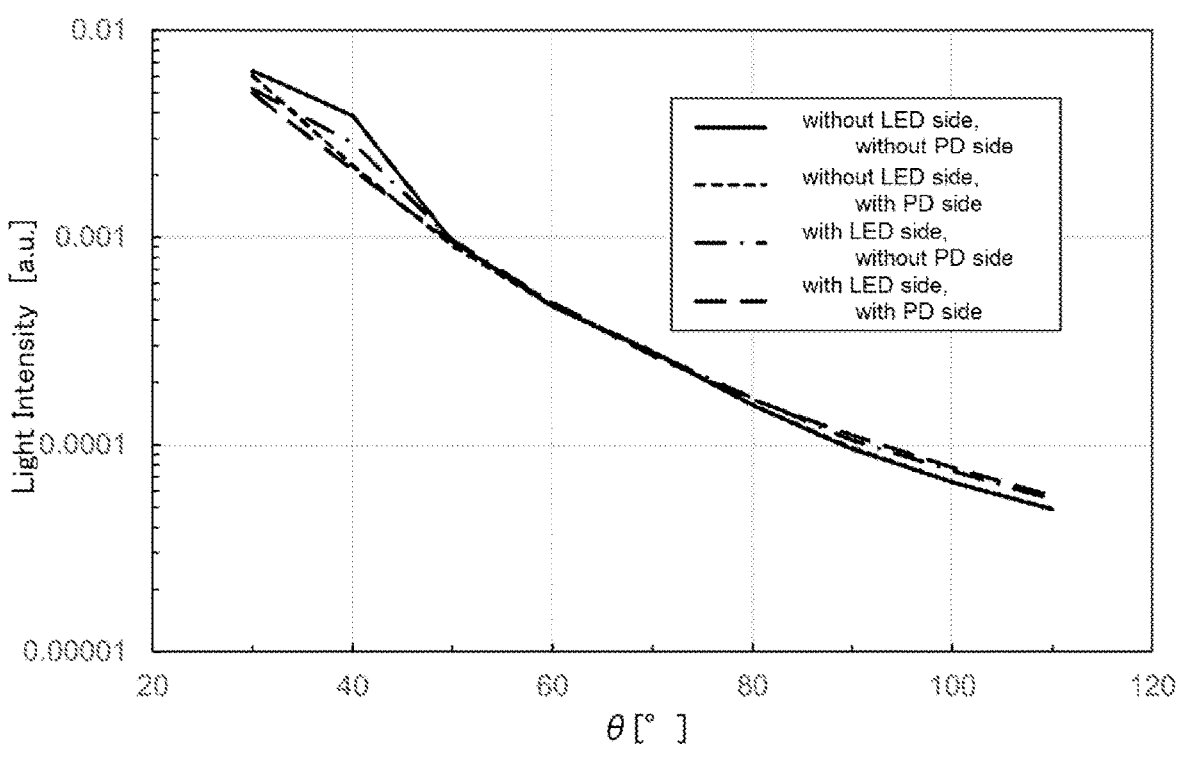
FIG. 14 is a graph illustrating the simulation results regarding to the relationship between (i) the angle θ representing the relative positions of the light emitting element and the light receiving element, and (ii) the intensity of light received by the light receiving element.
Figure 15:
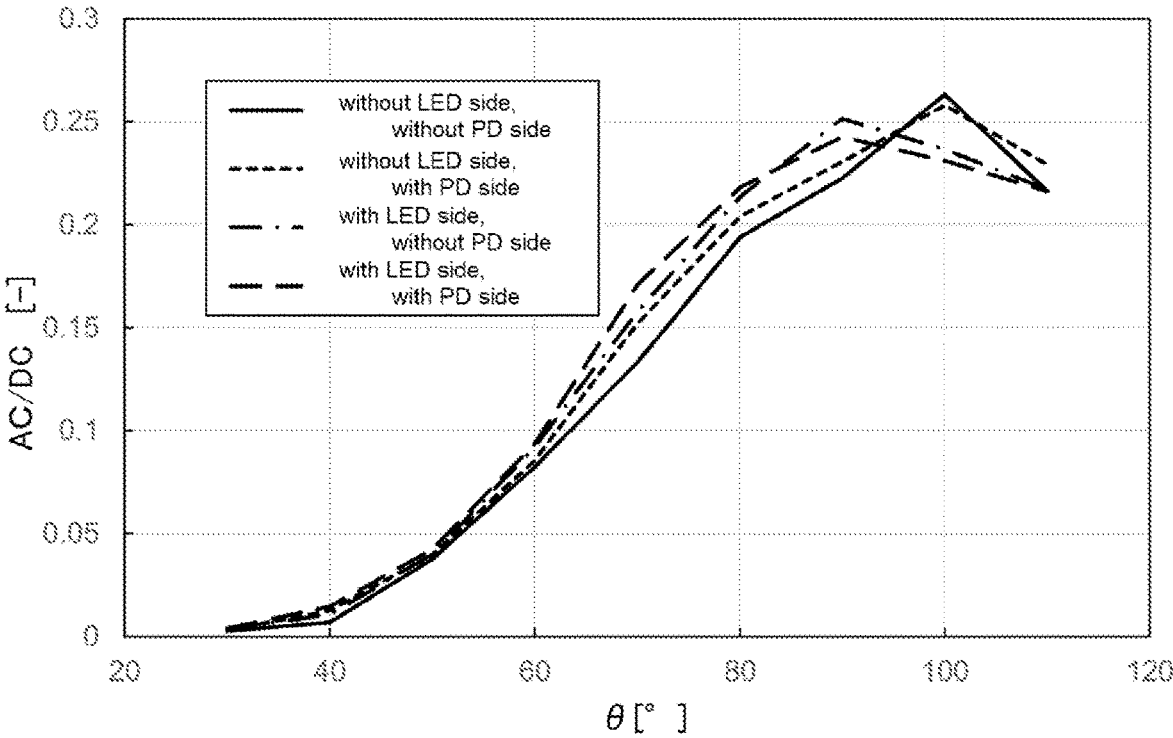
FIG. 15 is a graph illustrating the simulation results regarding to the relationship between (i) the angle θ representing the relative positions of the light emitting element and the light receiving element, and (ii) the perfusion index (AC/DC)

Based on the above-mentioned conditions, a simulation for multiple scattering system is performed to analyze the intensity of light reaching the light receiving element 17 by being multiple scattered in finger tissues when light having a near-infrared wavelength is emitted from the light emitting element 15 toward the center of the ring. FIGS. 14 and 15 depict the results of the optical simulations. FIG. 14 depicts a graph illustrating the simulation results regarding to the relationship between the angle θ representing the relative positions of the light emitting element and the light receiving element, and the intensity of light received by the light receiving element. FIG. 15 depicts a graph illustrating the simulation results regarding to the relationship between the angle θ representing the relative positions of the light emitting element and the light receiving element, and the perfusion index (AC/DC), which will be described later. In addition, notes are given to explain the presence or absence of the optical elements 16, 18 in the models. Here, the solid line indicates a case where both of the first optical element 16 and the second optical element 18 are not provided. The dotted line indicates a case where only the second optical element 18 is provided as the PD side. The dashed line indicates a case where only the first optical element 16 is provided as the LED side. Lastly, the broken line indicates a case where both of the first optical element 16 and the second optical element 18 are provided as the LED side and the PD side.

As depicted in FIG. 16, it is confirmed that, in a case that the light emitting element 15 is provided with the first optical element 16, the directivity is enhanced, and consequently it becomes possible to emit light having a high intensity. Also, it is confirmed that light having a higher luminous intensity may be emitted to the arterioles 506 with the same power consumption in comparison with the case where the first optical element 16 is not provided. In some embodiments, such a configuration may be adopted to such a case where the arteriole 506 existing in the deep region of biological tissues is irradiated as the illumination target. In addition, for the wearable device 1 which is required to be formed in a small size with a light weight, it becomes possible to make the secondary battery 415 compact in size and reduce a frequency of charging of the secondary battery 415.

The light intensity (which corresponds to the PPG signal) detected in the light receiving element 17 includes the pulsation component (which is hereinafter referred to AC component) caused by the volume change corresponding to the pulsation of heart, and the direct current component (which is hereinafter referred to DC component) composed of light reflected and/or scattered back from tissues (such as the skin, subcutaneous fat, bone, veins, etc.) other than the pulsation components. It is observed that the AC component and the DC component have a relation of AC≪DC. The AC/DC ratio of the AC component and the DC component is known as the Perfusion Index (which is abbreviated to PI). In general, the object of the wearable device 1 which is configured to measure vital signs based on the PPG signals is to increase the PI or the AC/DC ratio. In this simulation, the AC component is defined as a sum of the intensities of light which is emitted from the light-emitting device 15, passes through the arterioles 506 existing in the deep region of the subcutaneous tissues, and then arrives at the light-receiving device 17. In addition, the DC component is defined as a sum of the intensities of light which is emitted from the light-emitting device 15 and, immediately after this, arrive at the light-receiving device 17.

As depicted in FIG. 13, it is confirmed that the intensity of the received light becomes to decrease exponentially as the angle θ becomes large and as the distance between the light emitting element 15 and the light receiving element 17 becomes large. This might be attributed to the absorption of light by the living tissues in the finger. Further, as depicted in FIG. 14, it is confirmed that the AC/DC ratio becomes to increase as the distance between the light emitting element 15 and the light receiving element 17 becomes large under a condition of the angle θ which is in a range of from approximately 90° to 10°.

It can be said that in a region where the angle θ is small, a detectable amount of the light intensity is high so that it becomes possible to obtain a predetermined intensity of the detected light with less power consumption of the LED. Accordingly, such an embodiment may be applied to the wearable device 1 which is required to be formed in small size. It is considerable that a reflective type PPG sensor is made into a form of a single PPG sensor by mounting the light emitting element 15 and the light receiving element(s) 17 on the same board according to the characteristics of such living tissues. However, it can be seen that, in the region where the angle θ is small, the AC/DC ratio becomes small and also the rate of the light arriving at the light receiving element 17 passing through the deep region of finger tissues where the arterioles 506 exist becomes extremely small. In addition, the blood volume pulse is susceptible to external pressure in the region where the angle θ is small, because of the AC component based on the narrow arterioles near the dermis 502. Therefore, it can be said that it is not necessary to sufficiently reduce the angle θ in a case that the wearable device 1 is configured as a ring-type device.

In the region where the angle θ is large, the AC/DC ratio is large and the rate of the light arriving at the light receiving element 17 passing through the deep region of finger tissues where the arterioles 506 exist is large. Therefore, it can be said that it is suitable for the purpose of measuring the blood volume pulses at proper arterioles 506 of the palm side. However, it is found that in a case where the angle θ exceeds approximately 90° or 100°, the stability of the PPG signal could be deteriorated. It is considerable that it might be caused by the absorption of light by biological tissues including a bone and a tendon. Therefore, on the basis of the features of such living tissues, it is conceivable that, in a case of the permeation type PPG sensor, the blood volume pulses should be measured at a fingertip of not having a bone or at an ear droop, etc. However, in such a case of the permeation type PPG sensor, a detectable amount of light intensity is small. As a result, in the region where the angle θ is large, it is required to further increase the power consumption of the LED in order to obtain higher light intensity. Therefore, an angle θ that is too high need not to be applied to the ring-type wearable device 1 from the viewpoint of securing electric power.

From the above, in a case of the ring-type wearable device 1, the angle θ indicating the positional relationship between the light emitting element 15 and the light receiving element 17 may be formed as a quasi-transmission type which is between the reflection diffusion type and the transmission type. In addition, it can be said that the angle θ may be optimized since the intensity of the received light and the AC/DC ratio are in the relationship of trade-off.

The intensity of the received light is examined in detail, and it is confirmed that, in the angle range of 55° or more, the intensity of the received light of the wearable device 1 of having at least one of the optical elements 16, 18 is higher than that of the wearable device 1 of not having the optical elements 16, 18. With regard to the AC/DC ratio, it is confirmed that, with respect to all θ, the intensity of the received light of the wearable device 1 of having at least one of the optical elements 16, 18 is higher than that of the wearable device 1 of not having the optical elements 16, 18. It is confirmed that this trend becomes more prominent in the angle range (θ) of 55° or more, and it is estimated that the AC/DC ratio may significantly exceed 0.05. Thus, in some embodiments, the lower limit of θ may be 550 or more. The lower limit of θ may be such as for example, 60° or more, such as 62° or more, such as 64° or more, such as 66° or more, or such as 68° or more.

It is confirmed that, in a case that the first optical element 16 is included in the device, the AC/DC rate may be significantly improved in the angle range of 60° or more. However, it is also confirmed that, in a case that the first optical element 16 is included in the device, the AC/DC rate tends to be lowered in the angle range of 90° or more. In addition, it is also confirmed that, in a case that the first optical element 16 is not included in the device, the AC/DC rate tends to be lowered (to become unstable) in the angle range of 90° or more. Therefore, in some embodiments, the upper limit of θ may be 90° or less in order to reliably improve the AC/DC ratio by using the first optical element 16. The upper limit of θ may be such as for example, 85° or less, such as 80° or less, such as 78° or less, such as 76° or less, such as 74° or less, or such as 72° or less. For example, the angle θ may be made in a range of 70°±5°.

The embodiments according to the present technology have been concretely exemplified. These are given as examples which are not intended to limit the scope of the claims. A plurality of variations obtained by modifying or altering the examples illustrated above can be included in the techniques described in the claims.

In addition, in this specification, the description of numerical range (for example, N1 to N2) may arbitrarily include both of the angle range of "N1 or more and N2 or less", and the angle range of "more than N1 and less than N2."

The present disclosure is not limited to the above-described embodiments, and various modifications can be included therein. For example, the above-described examples are described in detail for the purpose of illustrating the present disclosure clearly, and are not necessarily limited to those comprising all the described configurations. It is also possible to replace a part of the configuration of one embodiment to the configuration of another embodiment, it is also possible to add the configuration of one embodiment to the configuration of another embodiment. Further, it is possible to add, delete, or replace a part of the configuration of each embodiment.

Further, each configuration, functions, processing unit, processing means, etc., described above, some or all of them, for example, may be realized by hardware by designing an integrated circuit, etc. In addition, each of the above-described configurations, functions, etc., may be implemented by software by interpreting and executing a program with which respective functions can be realized by the processor. Information capable of realizing various functions (such as the programs, tables, files, etc.) may be stored in the storing device such as the memory, hard disk, SSD, etc.; or in the recording medium such as the IC card, SD card, DVD, etc.

As stated above, the control lines and/or information lines are illustrated where an indication is thought to be necessary. However, not all control lines or information lines may not be illustrated on the product. In practice, almost all configurations may be thought to be interconnected with each other. The above-described embodiments shall contain at least the configurations written in the claims. For example, the claims may include the following configurations such as:

(1) A wearable device is provided so as to include a ring body having a shape of a ring; a light emitting element which is disposed in the ring body, and is configured to emit a light toward a center side of the ring; and a first optical element which is disposed in the ring body closer to the center side of the ring relative to the light emitting element, and is configured to change a direction of travel of the light to a direction in which a directional angle of the light is narrowed (in other words, a first optical element is configured to change a direction of travel of the light to a direction narrowing a directional angle of the light). In addition, the ring body includes a protrusion on an inner peripheral surface of the ring body, and a part of the protrusion is formed to protrude closer to the center side of the ring than another part of the inner peripheral surface where the first optical element is not disposed.

(2) In the wearable device according to (1), an end of the first optical element on, the center side of the ring may be positioned closer to the substantially center side of the ring than the inner peripheral surface.

(3) In the wearable device according to (1) or (2), the first optical element may be configured to have a directional angle of 600 or less.

(4) In the wearable device according to any one of (1) to (3), the first optical element may include a reflective surface, an end of the reflective surface, that is closer to the substantially center side of the ring, being positioned farther from a radius line that connects the substantially center of the ring and the light emitting element than an opposite end of the reflective surface.

(5) In the wearable device according to (4), the reflective surface may have a shape of a paraboloid.

(6) In the wearable device according to (4) or (5), the reflective surface may have a shape of a paraboloid of revolution around the radius line.

(7) In the wearable device according to any one of (4) to (6), the optical element may include an element body and a reflective film provided on the element body, and the reflective surface may be constituted by the reflective film.

(8) In the wearable device according to (7), the reflective film may comprise a metal film.

(9) In the wearable device according to any one of (1) to (8), a top part of the protrusion may have a flat surface (i.e. the protrusion has a flat top surface).

(10) In the wearable device according to any one of (1) to (9), a height of the protrusion may be 5% or more and 10% or less of an inner diameter of the ring (i.e. the height of the protrusion is in a range of 5 to 10% of an inner diameter of the ring).

(11) In the wearable device according to any one of (1) to (10), a thickness of a part of the ring body, covering the first optical element, may not be more than 0.5 mm.

(12) The wearable device according to any one of (1) to (11) may further include a light receiving element which is disposed in the ring body, and is configured to detect light; and a second optical element which is disposed in the ring body closer to the substantially center side of the ring relative to the light receiving element, and is configured to guide the light emitted by the light emitting element toward the light receiving element. The light emitting element and the light receiving element may be arranged such that an angle formed between (i) a line going through a substantially center of the ring and the light emitting element and (ii) a line going through the substantially center of the ring and the light receiving element is 550 or more and 90° or less.

(13) In the wearable device according to (12), a height of the first optical element extending around the light emitting element along a radius line connecting the first optical element and the substantially center of the ring may be larger than a height of the second optical element extending around the light receiving element along a radius line connecting the second optical element and the substantially center of the ring.

(14) In the wearable device according to any one of (1) to (13), the light emitting element may include a plurality of light emitting diodes configured to generate a plurality of light beams having same wavelength or different wavelengths.

(15) In the wearable device according to any one of (1) to (14), the light emitting element may include a green light emitting diode configured to generate a light having a center wavelength of 500 nm or more and 600 nm or less.

(16) In the wearable device according to any one of (1) to (15), the light emitting element may include (i) a light emitting diode configured to generate a light having a center wavelength of 630 nm or more and 690 nm or less and (ii) a light emitting diode configured to generate a light having a center wavelength of 810 nm or more and 990 nm or less.

(17) In the wearable device according to any one of (1) to (16), the ring body may include an exterior member which is disposed at an outer peripheral side of the ring body, and is configured to have a recessed part facing the substantially center side of the ring; and a sealing resin member which is disposed integrally with the exterior member closer to the center side of the ring than the exterior member. The light emitting element and the first optical element may be disposed in the recessed part and sealed by the sealing resin member.

(18) In the wearable device according to (17), the first optical element may be disposed so as to protrude from the exterior member toward the substantially center side of the ring.

(19) Also, a wearable device is provided so as to include a ring body which has a shape of a ring; a light receiving element which is disposed in the ring body, and is configured to detect light; and a second optical element which is disposed in the ring body closer to a center side of the ring (such as an approximately center of a ring, nearly center of a ring, almost completely center of a ring, completely center of a ring) relative to the light receiving element, and is configured to guide the light toward the light receiving element. The ring body includes a protrusion on an inner peripheral surface of the ring body where the second optical element is disposed, and a part of the protrusion is more protruding closer to the center side of the ring than another part of the inner peripheral surface where the second optical element is not disposed. In other word, the ring body includes a protrusion on an inner peripheral surface of the ring body, a part of the protrusion being formed to protrude closer to the substantially center side of the ring than another part of the protrusion where the second optical element is not disposed.

(20) Also, a health management system is provided so as to include a wearable device according to claim (1) or (19); a controller for calculating, based on biometric information which is acquired from the wearable device attached on a living body, health management information comprising at least one of heart rate, blood oxygen saturation level, blood pressure, and blood sugar level, by using photoplethysmogram (PPG); and an output unit for outputting the health management information.

(21) Also, a method for managing health is provided so as to include the steps of (i) calculating, based on biometric information which is acquired from a wearable device according to claim (1) or (19) by attaching the wearable device on a living body, health management information comprising at least one of heart rate, blood oxygen saturation level, blood pressure, and blood sugar level, by using photoplethysmogram (PPG); and (ii) outputting the health management information.

(22) In the method according to (21), the wearable device may be configured as a ring type device; and the living body may be a human finger.

What is claimed is:

1. A wearable device in a form of a ring configured to be worn on a finger, the wearable device comprising:

a ring body having a shape of a ring;

a light emitting element disposed in the ring body, configured to emit a light toward a center side of the ring;

a first optical element disposed in the ring body closer to the center side of the ring relative to the light emitting element, the first optical element being configured to change a direction of travel of the light to a direction in which a directional angle of the light is narrowed;

a light receiving element disposed in the ring body, configured to detect a light; and a second optical element disposed in the ring body closer to the center side of the ring relative to the light receiving element, the second optical element being configured to guide the light emitted by the light emitting element toward the light receiving element, wherein the ring body includes a protrusion on an inner peripheral surface of the ring body where the first optical element is disposed, a part of the protrusion being formed to protrude closer to the center side of the ring than another part of the inner peripheral surface where the first optical element is not disposed, and wherein the light emitting element and the light receiving element that are adjacent to each other are disposed such that an angle formed between a line segment connecting the center of the ring and the light emitting element and a line segment connecting the center of the ring and the light receiving element is between 55° and 90°.

2. The wearable device according to claim 1, wherein an end of the first optical element on the center side of the ring is positioned closer to the center side of the ring than the inner peripheral surface.

3. The wearable device according to claim 1, wherein the first optical element is configured to have a directional angle of 60° or less.

4. The wearable device according to claim 1, wherein the first optical element includes a reflective surface, an end of the reflective surface, that is closer to the substantially center side of the ring, being positioned farther from a radius line that connects the substantially center of the ring and the light emitting element than an opposite end of the reflective surface.

5. The wearable device according to claim 4, wherein the reflective surface has a shape of a paraboloid.

6. The wearable device according to claim 4, wherein reflective surface has a shape of a paraboloid of revolution around the radius line.

7. The wearable device according to claim 4, wherein the optical element includes an element body and a reflective film provided on the element body, and wherein the reflective surface is constituted by the reflective film.

8. The wearable device according to claim 7, wherein the reflective film comprises at least one of a metal film and a dielectric multi-layered film.

9. The wearable device according to claim 1, wherein the protrusion has a flat top surface.

10. The wearable device according to claim 1, wherein a height of the protrusion is 5% or more and 10% or less of an inner diameter of the ring.

11. The wearable device according to claim 1, wherein a thickness of a part of the ring body, covering the first optical element, is not more than 0.5 mm.

12. The wearable device according to claim 1, wherein a height of the first optical element extending around the light emitting element along a radius line connecting the first optical element and the substantially center of the ring is larger than a height of the second optical element extending around the light receiving element along a radius line connecting the second optical element and the substantially center of the ring.

13. The wearable device according to claim 1, wherein the light emitting element includes a plurality of light emitting diodes configured to generate a plurality of light beams having same wavelength or different wavelengths.

14. The wearable device according to claim 1, wherein the light emitting element includes a green light emitting diode configured to generate a light having a center wavelength of 500 nm or more and 600 nm or less.

15. The wearable device according to claim 1, wherein the light emitting element includes a light emitting diode configured to generate a light having a center wavelength of 630 nm or more and 690 nm or less and a light emitting diode configured to generate a light having a center wavelength of 810 nm or more and 990 nm or less.

16. The wearable device according to claim 1, wherein the ring body includes:

an exterior member disposed at an outer peripheral side of the ring body, being configured to have a recessed part facing the center side of the ring; and a sealing resin member disposed integrally with the exterior member closer to the center side of the ring than the exterior member, wherein the light emitting element and the first optical element are placed in the recessed part and sealed by the sealing resin member.

17. The wearable device according to claim 16, wherein the first optical element is disposed so as to protrude from the exterior member toward the center side of the ring.

18. A health management system, comprising:

a wearable device according to claim 1 a controller configured to calculate, by a volumetric pulse wave method, based on biometric information which is acquired from the wearable device attached on a living body, health management information comprising at least one of a heart rate, a blood oxygen saturation level, a blood pressure, and a blood sugar level; and an output unit configured to output the health management information.

19. A method for managing health, comprising:

calculating, by using photoplethysmogram, based on biometric information which is acquired from a wearable device according to claim 1, attached on a living body, health management information comprising at least one of a heart rate, a blood oxygen saturation level, a blood pressure, and a blood sugar level; and outputting the health management information.

20. The wearable device according to claim 1, wherein the ring body comprises:

an outer casing portion that forms an outer periphery of the ring body and having a recess on a center side of the ring; and a sealing resin portion that forms an inner periphery of the ring body by being integrally disposed on the center side of the ring relative to the outer casing portion, wherein the outer casing portion includes at least one of a metal, a ceramic, and a high-strength resin, and wherein the sealing resin portion includes a transparent resin material.

21. A wearable device in a form of a ring configured to be worn on a finger, the wearable device comprising:

a ring body having a shape of a ring;

a light emitting element disposed in the ring body, configured to emit a light toward a center side of the ring;

a first optical element disposed in the ring body closer to the center side of the ring relative to the light emitting element, the first optical element being configured to change a direction of travel of the light to a direction in which a directional angle of the light is narrowed;

a light receiving element disposed in the ring body, configured to detect a light; and a second optical element disposed in the ring body closer to a center side of the ring relative to the light receiving element, the second optical element configured to guide the light toward the light receiving element, wherein the ring body includes a protrusion on an inner peripheral surface of the ring body where the second optical element is disposed, a part of the protrusion being protruding closer to the center side of the ring than another part of the inner peripheral surface where the second optical element is not disposed, and wherein the light emitting element and the light receiving element that are adjacent to each other are disposed such that an angle formed between a line segment connecting the center of the ring and the light emitting element and a line segment connecting the center of the ring and the light receiving element is between 55° and 90°.

\* \* \* \* \*